(12) United States Patent
Dasgupta

(10) Patent No.: US 8,513,374 B2
(45) Date of Patent: Aug. 20, 2013

(54) BIOCOMPATIBLE AND BIODEGRADABLE POLYMERS FROM RENEWABLE NATURAL POLYPHENOLS

(76) Inventor: Falguni Dasgupta, Bozeman, MT (US)

( * ) Notice: Subject to any disclaimer, the term of this patent is extended or adjusted under 35 U.S.C. 154(b) by 0 days.

(21) Appl. No.: 13/498,886

(22) PCT Filed: Sep. 30, 2010

(86) PCT No.: PCT/US2010/050831
§ 371 (c)(1),
(2), (4) Date: Mar. 28, 2012

(87) PCT Pub. No.: WO2011/041487
PCT Pub. Date: Apr. 7, 2011

(65) Prior Publication Data
US 2012/0184682 A1    Jul. 19, 2012

Related U.S. Application Data

(60) Provisional application No. 61/247,284, filed on Sep. 30, 2009, provisional application No. 61/360,728, filed on Jul. 1, 2010.

(51) Int. Cl.
*C08G 64/00*    (2006.01)
*C08G 63/18*    (2006.01)

(52) U.S. Cl.
USPC ............ 528/195; 525/277; 525/453; 528/75; 528/85; 528/196; 528/204; 558/268; 568/316; 568/646

(58) Field of Classification Search
USPC .............. 525/277, 453; 528/75, 85, 196, 528/204; 558/268; 568/316, 646
See application file for complete search history.

(56) References Cited

U.S. PATENT DOCUMENTS

| | | |
|---|---|---|
| 3,706,713 A | 12/1972 | Hull et al. |
| 3,966,840 A | 6/1976 | Edl et al. |
| 4,326,049 A | 4/1982 | Rasmussen |
| 4,686,266 A | 8/1987 | Tang |
| 5,160,783 A | 11/1992 | Nemoto et al. |
| 5,221,761 A | 6/1993 | Jen et al. |
| 5,281,419 A | 1/1994 | Tuan et al. |
| 5,312,871 A | 5/1994 | Mardare et al. |
| 5,412,061 A | 5/1995 | King, Jr. et al. |
| 5,753,726 A | 5/1998 | Reuter et al. |
| 5,969,060 A | 10/1999 | Arai |
| 6,355,767 B1 | 3/2002 | Takagi |
| 6,562,433 B1 | 5/2003 | Ishida et al. |
| 6,605,691 B1 | 8/2003 | Gross et al. |
| 7,009,025 B2 | 3/2006 | Kosaka |
| 7,148,312 B2 | 12/2006 | Kim et al. |
| 7,235,598 B1 | 6/2007 | Zobel et al. |
| 7,288,608 B2 | 10/2007 | Bowman et al. |
| 7,354,978 B2 | 4/2008 | Nishitani |
| 7,365,148 B2 | 4/2008 | Ono et al. |
| 7,741,375 B2 | 6/2010 | Benz et al. |
| 7,772,296 B2 | 8/2010 | Garey, Jr. |
| 8,133,939 B2 | 3/2012 | Isozaki et al. |
| 2004/0185029 A1 | 9/2004 | Tang |
| 2006/0173065 A1 | 8/2006 | Bezwada |
| 2008/0076821 A1 | 3/2008 | Di Mauro |
| 2008/0095866 A1 | 4/2008 | Declercq et al. |
| 2008/0146776 A1 | 6/2008 | Liu et al. |
| 2009/0029058 A1 | 1/2009 | Grasboeck et al. |
| 2009/0142537 A1 | 6/2009 | Hong et al. |
| 2010/0063209 A1 | 3/2010 | Bowman et al. |
| 2010/0150832 A1 | 6/2010 | Papisov |
| 2010/0210809 A1 | 8/2010 | Simon et al. |
| 2012/0220749 A1* | 8/2012 | Dasgupta ................ 528/226 |

FOREIGN PATENT DOCUMENTS

| | | |
|---|---|---|
| DE | 3506472 A1 | 8/1986 |
| EP | 0535261 A1 | 4/1993 |
| WO | 2009036229 A1 | 3/2009 |

OTHER PUBLICATIONS

Allcock, Harry R., "Inorganic-Organic Polymers", Adv. Mater, (1994) 6, No. 2, pp. 106-115.
Allcock, H.R., "Macromolecules", Amer. Chemical Society, (Sep. 1983) vol. 16, No. 9, pp. 1401-1406.
Braniste, Viorica et al., "Impact of oral bisphenol a at reference doses on intestinal barrier function intestinal barrier function and sex differences after perinatal exposure in rats", PNAS, (Jan. 2010) vol. 107, No. 1, pp. 448-453.
Duncan, R., "Designing polymer conjugates as lysosomotropic nanomedicines", Biochemical Society Transactions (2007) vol. 35, part 1, pp. 56-60.
Dunn, R.L. and Ottenbrite, R.M., Polymeric Drugs and Drug Delivery Systems, (Eds), ACS Symp. Series, 469 (1991).
Erickson, Britt E., "Bisphenol a Battle", C&EN Washington, www.cen-online.org, (Nov. 2008) pp. 42-45.
Gibson, L., "Baby's Toxic Bottle; Bisphenol a leaching from popular baby bottles", Environmental California Research and Policy Center (2007); ACS Chem. Biol., 3 (2008) 167.
Int'l Searching Authority/US, "Int'l Search Report and Written Opinion", (Nov. 2010) US Patent & Trademark Office, PCT,Int'l Appln. No. PCT/US10/50831.
Chemical & Engineering News, "BPA Craziness", vol. 88, No. 9, pp. 5 (2010).
Chemical & Engineering News, "FDA Raises Flag on Bisphenol A", www.cen-online.org, pp. 8, Jan. 25, 2010.
Chemical & Engineering News (Voith, Melody), "Can Conundrum—Chemists come up short in attempts to remove Bisphenol A from food can liners", www.cen-online.org, pp. 28-29, (2009).
Jain, Rajeev, et al., "Controlled Drug Delivery by Biodegradable Poly(Ester) Devices: Different Preparative Approaches", Drug Development and Industrial Pharmacy, (1998) 24(8), pp. 703-727.

(Continued)

*Primary Examiner* — Terressa Boykin
(74) *Attorney, Agent, or Firm* — LeClairRyan

(57) ABSTRACT

This invention describes the use of resveratrol and curcumin, representatives of naturally occurring polyphenols, in their native form, after hydrogenation, and as their respective allyl derivatives, individually, in combination with themselves and other commercial monomers, to make representative varieties of polymers, e.g., polycarbonates (PC), polyurethanes (PU), co-polymers and biodegradable polymers.

10 Claims, 7 Drawing Sheets

(56) References Cited

OTHER PUBLICATIONS

Midori-Horiuti, Terumi et al., "Maternal Bisphenol a Exposure Promotes the Development of Experimental Asthma in Mouse Pups", Environmental Health Perspectives (Feb. 2010), vol. 118, No. 2, pp. 273-277.

Pillai, Omathanu et al., "Polymers in drug delivery", Next Generation Therapeutics, Current Opinion in Chemical Biology 2001, 5: pp. 447-451.

Richards, M., et al., "Evaluation of polyphosphates and polyphosphonates as degradable biomaterials", Jour. of Biomedical Materials Research (1991), vol. 25, pp. 1151-1167.

Shieh, L., et al., "Erosion of a new family of biodegradable polyanhydrides", Jour. of Biomedical Materials Research (1994), vol. 8, pp. 1465-1475.

Sinha, Vivek R., et al., "Bioabsorbable Polymers for Implantable Therapeutic Systems", Drug Development and Industrial Pharmacy, 24(12), pp. 1129-1138 (1998).

\* cited by examiner

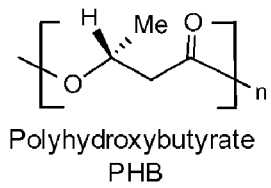
Polyhydroxybutyrate
PHB

FIG. 2A

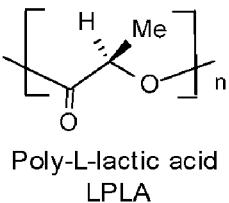
Poly-L-lactic acid
LPLA

FIG. 2B

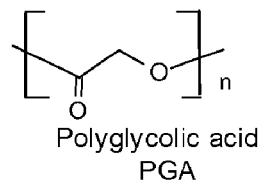
Polyglycolic acid
PGA

FIG. 2C

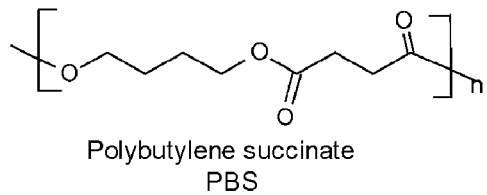
Polybutylene succinate
PBS

FIG. 2D

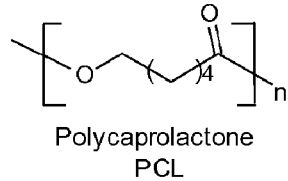
Polycaprolactone
PCL

FIG. 2E

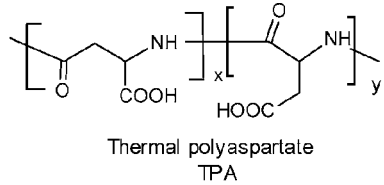
Thermal polyaspartate
TPA

FIG. 2F

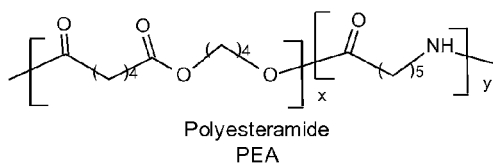
Polyesteramide
PEA

FIG. 2G

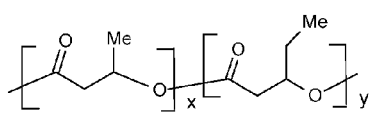
Polyhydroxybutyrate-co-hydroxyvalerate
PHBV (a Polyhydroxyalkanoate)

FIG. 2H

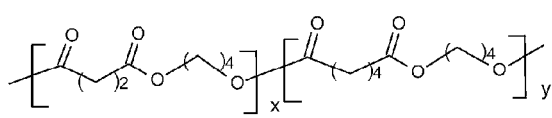
Poly (butylene succinate adipate)
PBSA

FIG. 2I

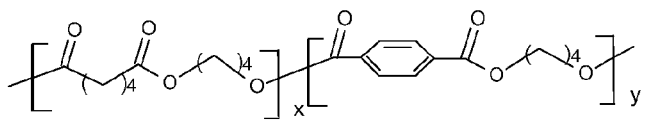
Poly (butyleneadipate-co-terephthalate)
PBAT (an aromatic copolyester)

FIG. 2J

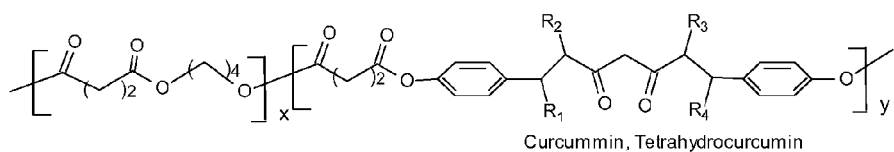
Biodegradable polyphenol polyester_
Generic example, e.g., Polybutylenesuccinate-co-poly(curcuminsuccinate)

Curcummin, Tetrahydrocurcumin

FIG. 2K

BIOCOMPATIBLE AND BIODEGRADABLE POLYMERS FROM RENEWABLE NATURAL POLYPHENOLS

RELATED APPLICATIONS

This application is a United States National Phase application which filing under 35 USC 371 of International Application No. PCT/US2010/050831 having an International Filing Date of 30 Sep. 2010 and entitled, "Biocompatible and Biodegradable Polymers From Renewable Natural Polyphenols", which claims the benefit of priority to U.S. Provisional Patent Application No. 61/247,284, filed on Sep. 30, 2009, and U.S. Provisional Patent Application No. 61/360,728, filed on Jul. 1, 2010, all of which are hereby incorporated by reference in their entirety.

BACKGROUND OF THE INVENTION

There is great need for degradable, environment friendly polymeric materials that are non-toxic to human health over their prolonged use. The demand for such polymers is particularly high as food packaging material as well as health and personal care products, especially where individuals or the consumable materials are exposed to the polymer over prolonged periods. Biodegradability without generating toxic by-products both in vivo and ex vivo is indeed desirable in all new polymers. Highly controversial phenolic compound Bisphenol A (BPA) and its analogs are commonly used monomers in making polymers for which demand for replacement has grown over the years [C&EN, January 25, 2010 8 and Mar. 1 2010 5; *Environmental health perspectives*, 118 (2010) 273-277; C&EN, Jul. 20, 2009 28; *Proceedings of the National Academy of Sciences of the United States of America*, 107 (2009) 448-453; C&EN, Dec. 15, 2008 31; C&EN, Nov. 17, 2008 42; Toxic Baby Bottles, Report by R. L. Gibson, 'Environment California Research and Policy Center' (2007); *ACS Chem. Biol.*, 3 (2008) 167; *Environmental Health Perspectives*, May 12, 2009; *Researcher*, 1(2009)90] and several countries have decided to take action on the side of caution. USFDA has expressed concern over the potential health effects of BPA in infants and children. Therefore, at the present time, the need to make polymers from renewable sources (especially non-petroleum sources) cannot be understated. However, finding a replacement is a challenge since, from the perspective of relevant industry, the 'new' material should ideally have properties that would conform/accommodate current manufacturing processes and have physicochemical characteristics of BPA while satisfying all health and environment related concerns.

SUMMARY OF THE INVENTION

Polyphenols occur abundantly in nature. A number of them are well known as active ingredients of food and nutritional supplements (Chart 1). Characteristically they possess phenolic hydroxyl function, like those present in BPA and its analogs, thus making them suitable for conversion to polymeric material. Therefore, these natural raw materials, as such and in their suitably modified forms, could be important starting compounds for making a wide variety of polymers with applications ranging from making environment friendly plastics to materials useful for drug delivery, coating of containers and medical devices as well as in personal care products.

Curcumin (CCM) and Resveratrol (RSVR), two well known polyphenolic compounds, are representative natural polyphenols. These are also hydrogenated to provide tetrahydrocurcumin (THCCM) and dihydroresveratrol (DHRSVR) respectively, two direct descendents which, having lost the double bonds present in their parent compounds, are more flexible and expected to provide polymeric compounds with physicochemical properties different from those made from their parent monomers under the same reaction conditions (FIG. 1). Allyl ethers and allyl carbonate derivatives of the above four compounds were also prepared for use as monomers.

CCM, with 'generic' structural similarity to controversial Bisphenol A undergoes reactions similar to bishenolic compounds and provides linear polymeric chains. On the other hand RSVR, representing other naturally occurring polyphenols, with phenolic hydroxyls directed non-linearly in space, polymerizes to give more complex polymer networks when undergoing similar polymerization reactions. Significantly, therefore, naturally occurring polyphenols, give polymers with different properties when undergoing the same chemical process, depending on the spatial configuration of their hydroxyl functions. It is understood that the final properties of such polymers will vary depending on the characteristic of the starting bi-/multi-functional polyphenol chosen for the purpose and the nature of the chemical linkages that will eventually constitute the end polymeric compound. Here we elaborate these observations by making polycarbonates (PC), polyurethanes (PU), block polymers having both PC and PU linkages, using CCM, THCCM, RSVR and DHRSVR as well as radical initiated polymers from their allyl carbonate derivatives. Thus, Curcumin (Diferuloyl methane, (E,E)-1,7-Bis(4-hydroxy-3-methoxy phenyl)-1,6-heptadiene-3,5-dione, GRAS designated); its hydrogenated product, Tetrahydrocurcumin (1,7- Bis (4-O-allyloxy carbonyl-3-methoxyphenyl)-heptane-3,5-dione), and trisphenolic compounds, Resveratrol (3, 5, 4'-Trihydroxy-trans-stilbene) and its hydrogenated product Dihydroresveratrol [1-(3,5 -dihyroxy phenyl)-2-(4-hydroxyphenyl)-ethane] were utilized to make polycarbonates (PC), polyurethanes (PU), polymers having both PC and PU linkages, and mixed polycarbonates (various combinations of CCM, THCCM, RSVR, DHRSVR and BPA). bis-Allyl carbonate derivatives of all four compounds were polymerized with Pentaerythritol mercapto acetate (PETMA) using free radical induced ene-thiol reaction to produce novel 3D polymers having biodegradable ester and carbonate linkages. Whereas allyl functionalized monomers have been chosen to exemplify application of 'thiol-ene' chemistry and make polymers from the chosen polyphenolic compounds, other functionalized monomers of the same polyphenols can be prepared which can then be polymerized to give differently linked polymers, for example, epoxy resins, polyamides, polyethers, among others. These new polymers should provide materials that will fulfill some of the current needs and find unique applications.

One embodiment of this invention is a synthetic polymer comprising at least one or more monomer units of at least one naturally occurring plant polyphenol or a derivative thereof. In another embodiment of the invention, the synthetic polymer comprises at least one chemical linkage of carbonate, ether, carbamate, urethanes, thiocarbamate, thioether, or ester. In a particular embodiment of the invention, the polymer is a homopolymer, co-polymer, block polymer, block co-polymer, grafted polymer, 3D polymer or interpenetrating polymer. In yet another embodiment of the invention, the polymer comprises at least one of the following polyphenols: Curcumin, a hydrogenated curcumin, Tetrahydrocurcumin, Resveratrol, hydrogenated Resveratrol, or DH-Resveratrol.

In another embodiment of this invention is a synthetic polymer comprising at least two, or at least three, or at least four, or at least about five, or at least about ten, or at least about 20, or at least about 50, or at least about 100, or at least about 150, or at least about 200, or at least about 250, or at least about 300, or at least about 350, or at least about 500, or at least about 750, or at least about 1000 monomer units of at least one naturally occurring plant polyphenol or a derivative thereof.

A further embodiment of the invention includes derivatives of a plant polyphenol, including Curcumin diallyl carbonate, Tetrahydrocurcumin diallyl carbonate, Resveratrol triallyl carbonate, Mono-O-allyl curcumin, Tetra-allyl curcumin, Di-allyl Tetrahydrocurcumin, Tetra-allyl Tetrahydrocurcumin, and Tri-O-allyl resveratrol.

In another embodiment of the invention is a synthetic polymer comprising at least one monomer unit of a polyphenol derivative such as: Curcumin diallyl carbonate, Tetrahydrocurcumin diallyl carbonate, Resveratrol triallyl carbonate, Mono-O-allyl curcumin, Tetra-allyl curcumin, Di-allyl Tetrahydrocurcumin, Tetra-allyl Tetrahydrocurcumin, and Tri-O-allyl resveratrol. In another embodiment of the invention, the synthetic polymer comprising a polyphenol derivative comprises at least one chemical linkage of carbonate, ether, carbamate, urethanes, thiocarbamate, thioether, or ester.

This invention also embodies the methods of making the polyphenol derivatives. In yet another embodiment, the invention includes methods of making polymers from naturally occurring plant polyphenols. In a further embodiment, the invention includes methods of making polymers from derivatives of naturally occurring plant polyphenols.

BRIEF DESCRIPTION OF THE DRAWINGS

Chart 1. Structures of some natural polyphenols and antioxidants.

FIGS. 2A-2K illustrates some usual biodegradable polymers for drug delivery, vis-it-vis a representative polymer using curcumin/tetrahydrocurcumin.

DETAILED DESCRIPTION OF THE INVENTION

Figure 1A:
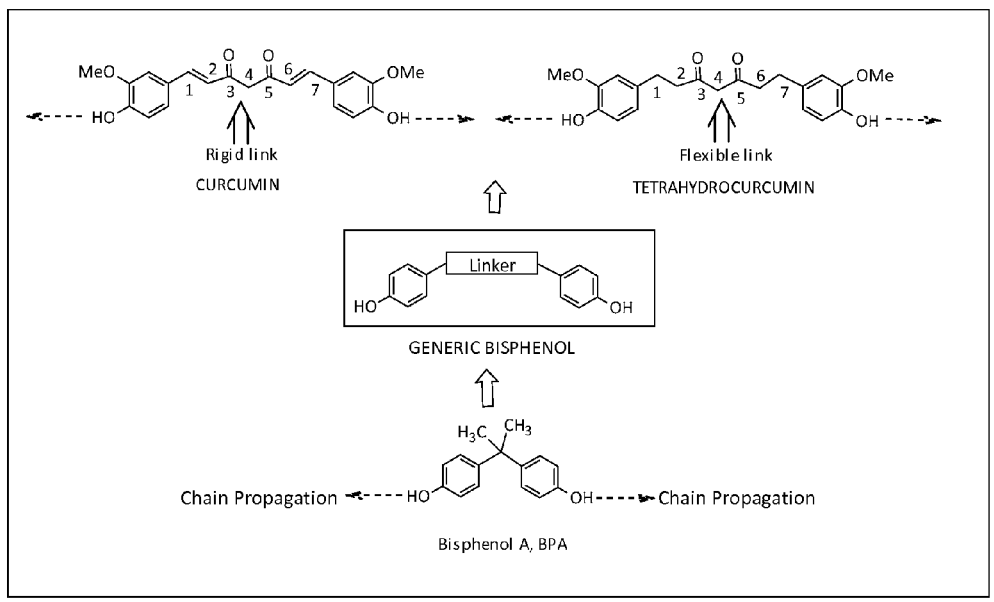
FIGS. 1A-1B illustrate structures of curcumin with Bisphenol A, tetrahydrocurcumin, resveratrol, a trishydroxyphenol (dashed arrows indicate the axis of chain elongation), and hydroresveratrol.
Figure 1B:
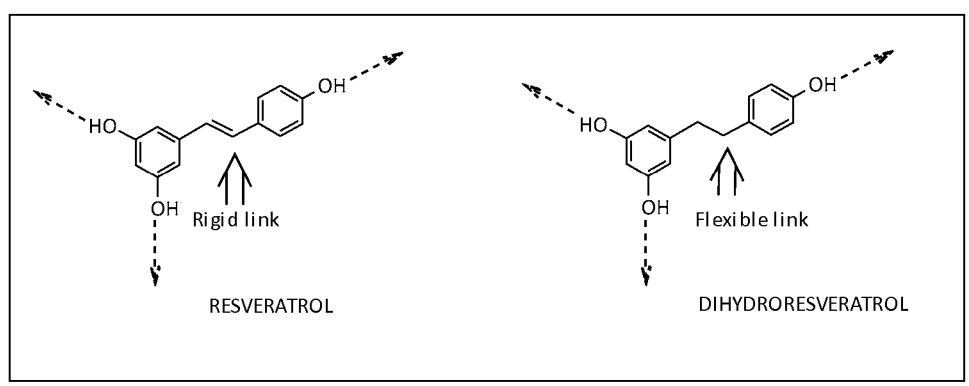
Figure 3A:
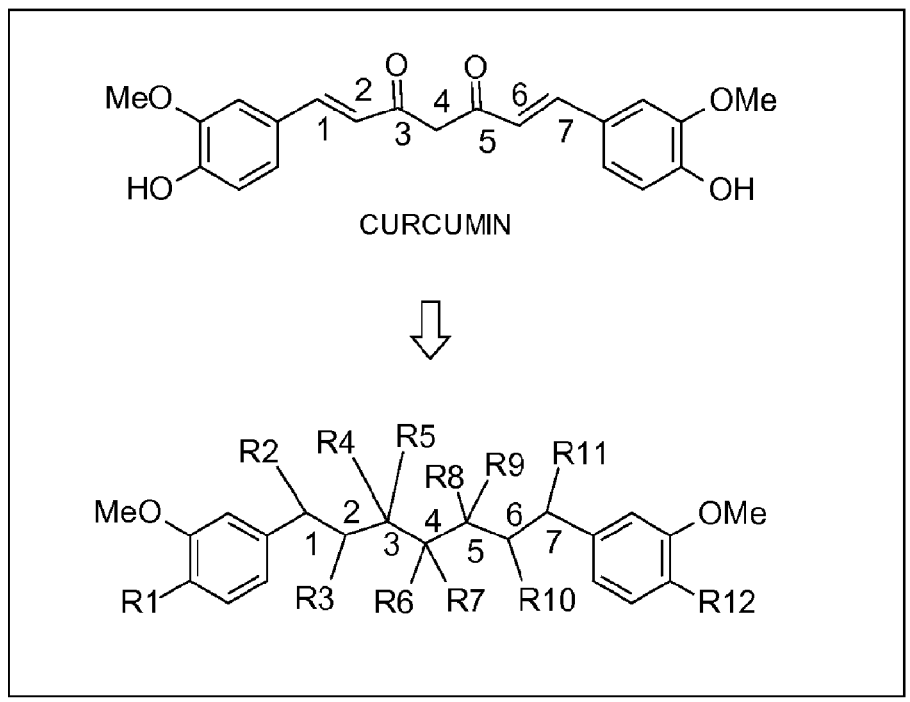
FIGS. 3A-3B illustrate generic structures of curcumin and resveratrol and chemical modifications envisaged, where R1-R12=independently, are same or a combination of functions such as and without limiting, amine, substituted amine, imine, substituted imine, halogen, hydroxyl, alkyl, alkylene, alkoxy, epoxide, ester, amide, methylene, carbocyclic ring, heterocyclic ring and substituted versions thereof.
Figure 3B:
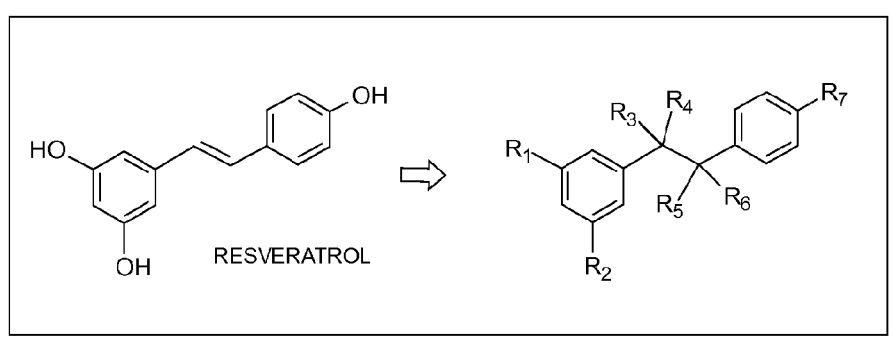
Figure 4A:
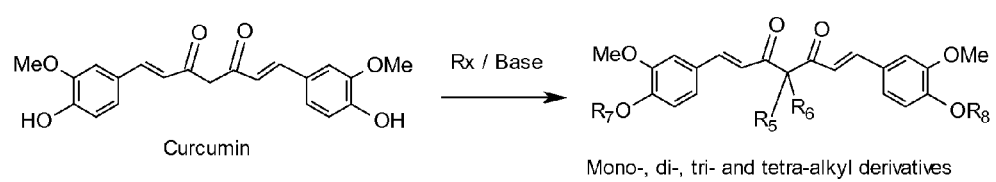
FIGS. 4A-4B illustrate alkylation reaction products of curcumin and tetrahydrocurcumin, where Rx is alkylating reagent, R, without limiting, can be alkyl, alkenyl, alkoxyalkyl, epoxyalkyl, aminoalkyl, carboxyalkyl, alkoxycarbonyl, arylalkyl, suitable oligomeric or macromolecular substrates and derivatives and substituted versions thereof, and x, is a leaving group represented by Cl, Br, I, methylsulfonyl, p-toluenesulfonyl, trifluoromethanesulfonyl, among others.
Figure 4B:
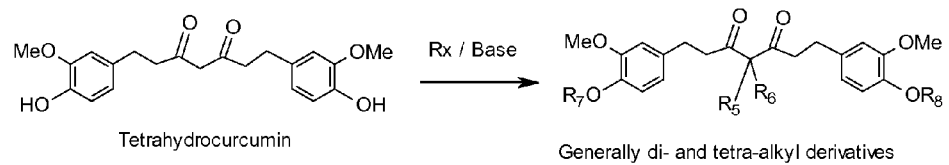
Figure 5:
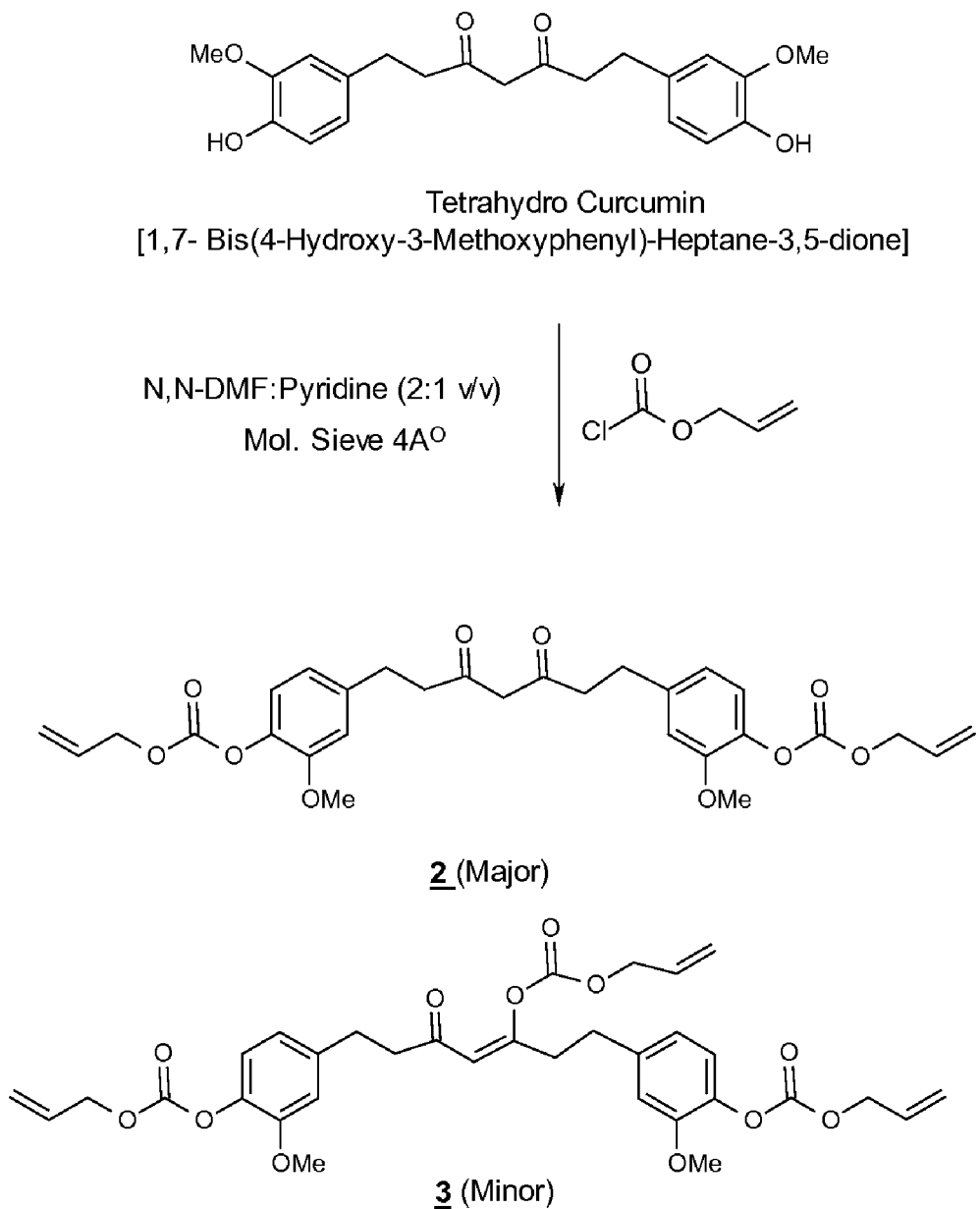
FIG. 5. Preparation of allyl carbonate derivatives: Synthesis of di-allyl carbonate derivative of tetrahydrocurcumin.
Figure 6:
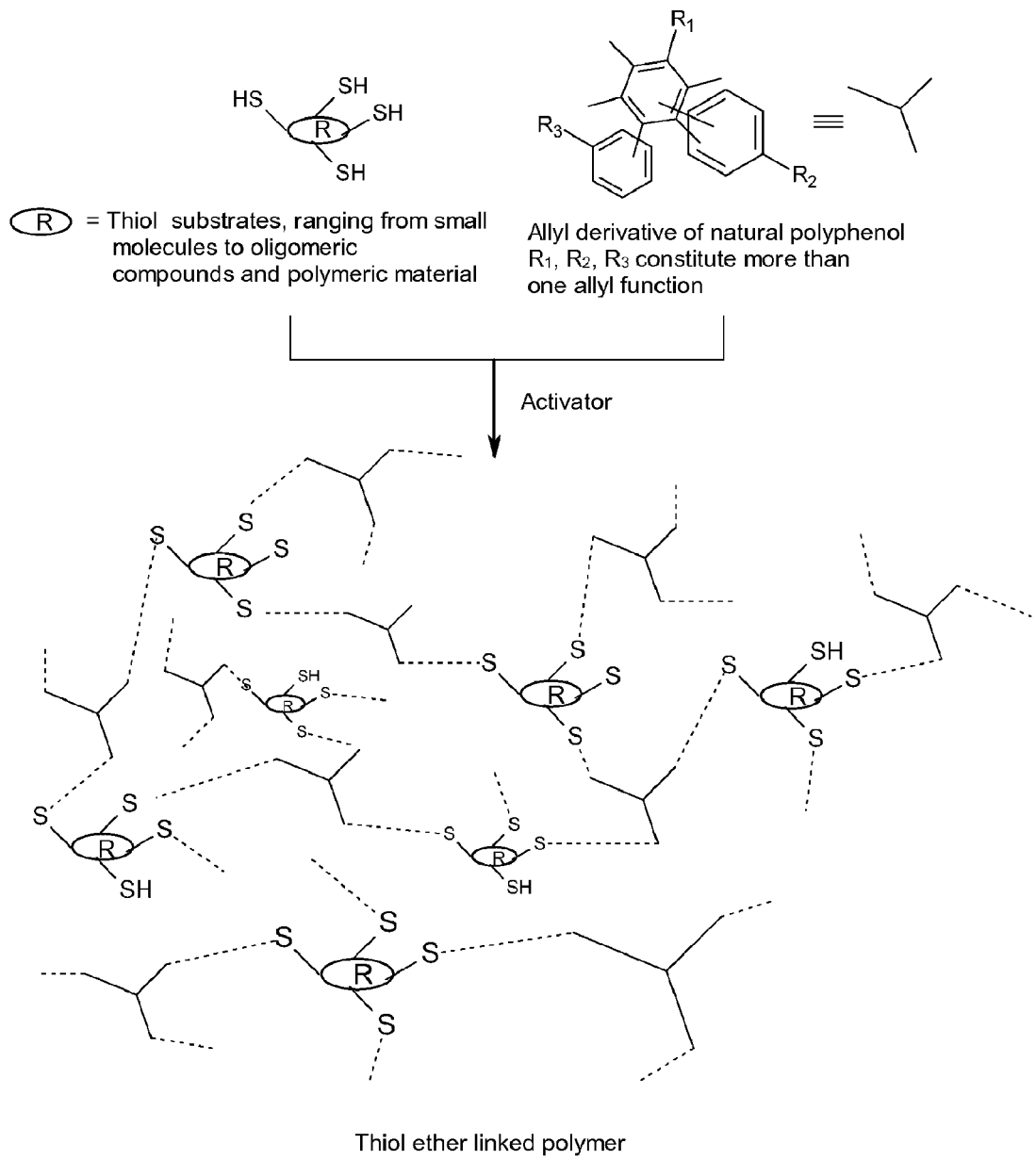
FIG. 6. Generic scheme representing polymerization of allyl derivatives of polyphemols with thiol substrates.
Figure 7:
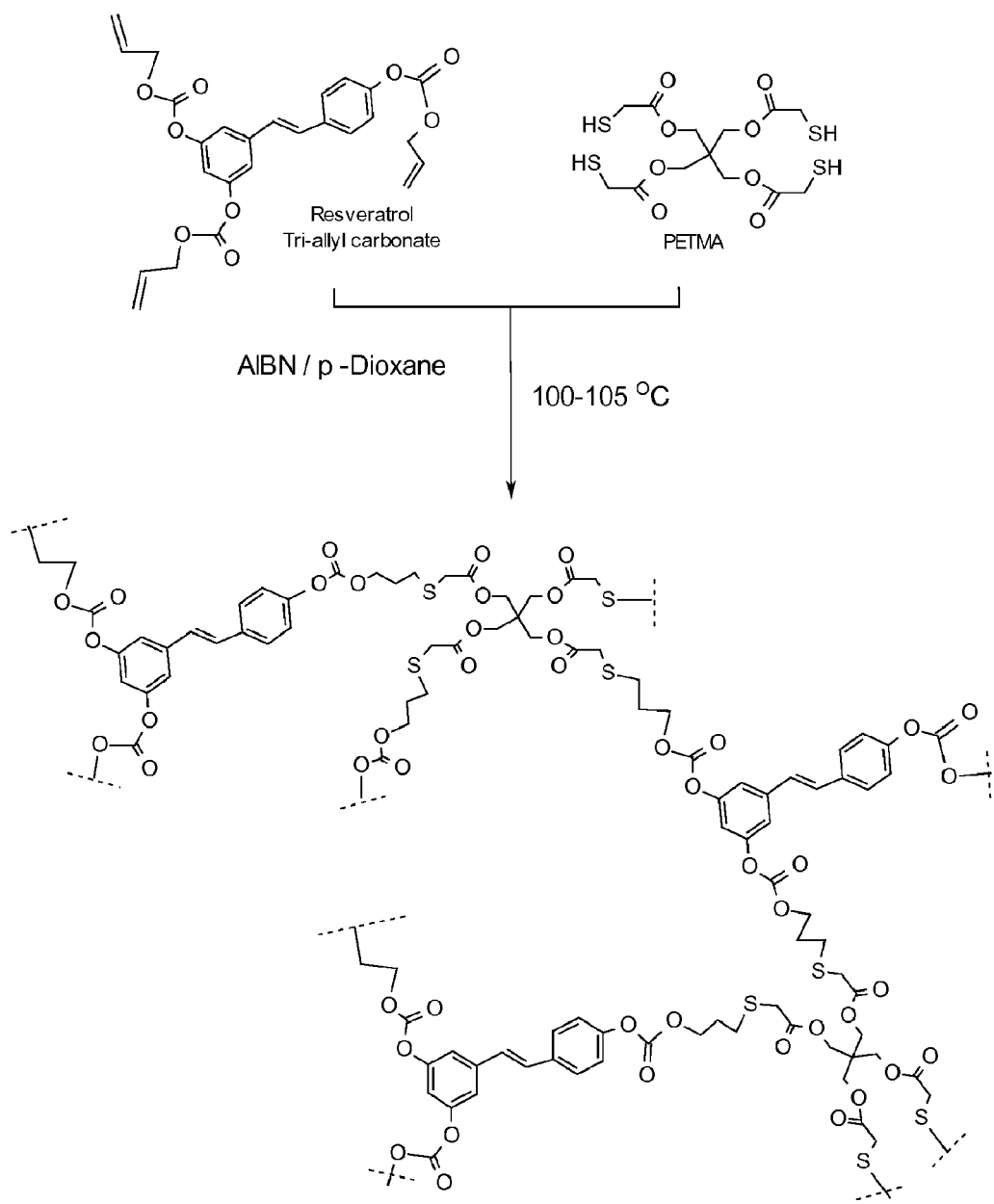
FIG. 7. Representative reaction of resveratrol triallyl carbonate with PETMA.

All documents cited are herein incorporated by reference in their entirety for all purposes. The citation of any document is not to be construed as an admission that it is prior art.

Typically polymers are repeating units of one or more chemical units joined together through chemical linkages. These chemical linkages and the nature of monomer units define the overall characteristics of the resulting polymer. Many polymer types have been made during the last 100 years, and more are being added every year in order to accommodate their growing demand in fields ranging from garments and personal care products to engineered goods, biotechnology and space science.

Currently there is universal demand for polymeric material that would not disturb the environment in the long run and be benign to human health while being biodegradable and made from renewable starting material. This has put tremendous pressure (on the polymer industy), to find substitutes that would fulfill some, if not all the required criteria. There is also popular awareness of health impact of polymers that has grown in the recent years, greatly affecting industries and businesses whose polymers are used in food, packaging and personal care, especially where individuals or the consumable materials are exposed to the polymer over prolonged periods. Typically these polymers are polycarbonates, copolycarbonates, mixed polymers and resins many of which are made using bisphenolic compounds, most commonly, Bisphenol A or BPA.

BPA is deeply imbedded in the products of modern society being used as the building block for polycarbonate plastic, in the manufacture of epoxy resins and other plastics, e.g., polysulfone, polyester-styrene, certain polyester resins. It has been used as an inert ingredient in pesticides, as a fungicide, antioxidant, flame retardant, rubber chemical, and polyvinyl chloride stabilizer. In several of its applications, BPA comes in intimate human contact, e.g., BPA-based polycarbonate is used as a plastic coating to prevent cavities for children's teeth as well as to coat metal cans to prevent the metal from contact with food contents, as plastic containers for storing food, baby bottles, water bottles, containers for juice, milk and water, micro-wave ovenware and eating utensils. Exposures to BPA also come from the use of films, sheets, and laminations; reinforced pipes; floorings; water-main filters; enamels and vanishes; adhesives; artificial teeth; nail polish; compact discs; electric insulators; and as parts of automobiles, certain machines, tools, electrical appliances, and office automation instruments. BPA contamination is currently widespread in the environment and found in measurable quantities in soils, rivers and estuaries.

Since BPA leaches out of all polymeric compositions used in the above applications, its repercussion on human health have been studied in detail and the result has led to concerns. Exposure to BPA has been implicated in possible incidence of asthma, allergy, estrogen related disorders, miscarriage, birth defects, breast cancer, sensitivity to other chemicals, prostate lesions, prostate cancer, insulin resistance. [O. George, Bj K. Bryant, R Chinnasamy, C. Corona, J. B. Arterburn and C. B. Shuster, *ACS Chem. Biol.*, 3 (2008) 167-179;M. Durando, L. Kass, J. Piva, C. Sonnenschein, A. M. Soto, E. H. Luque E H, et al., Environmental Health Perspectives, 115 (2007) 80-86; P. Alonso-Magdalena, S. Morimoto, C. Ripoll, E. Fuentes and A. Nadal, *Environmental Health Perspectives* 114 (2006) 106-112; T. J. Murray, M. V. Maffini, A. A. Ucci, C. Sonnenschein and A. M. Soto, Reproductive Toxicology, 23 (2006) 383-390; B. G. Timms, K. L. Howdeshell, L. Barton, S. Bradley, C. A. Richter and F. S. vom Saal, PNAS, 102 (2005) 7014-7019; K. Kubo, O. Arai, M. Omura, R. Wantanabe, R. Ogata, and S. Aou, Neuroscience Research, 45 (2003) 345-356; P. A. Hunt, K. E. Koehler, M. Susiarjo, C. A. Hodges, A. Ilagan, R. C. Voigt, S. Thomas, B. F. Thomas and T. J. Hassold, Current Biology, 13 (2003) 546-553; H. Masuno, T.

Kidani, K. Sekiya, K. Sakayama, T. Shiosaka, H. Yamamoto and K. Honda, *Journal of Lipid Researh*, 3 (2002) 676-684; Y. B. Wetherill, C. E. Petre, K. R. Monk, A. Puga, and K. E. Knudsen, *Molecular Cancer Therapeutics*, 1(2002) 515-524; B. S. Rubin, M. K. Murray, D. A. Damassa, J. C. King and A. M. Soto, *Environmental Health Perspectives*, 109 (2001) 675-680; J. G. Ramos, J. Varayoud, C. Sonnenschein, A. M. Soto, M. Múnoz de Toro and E. H. Luque, *Biology of Reproduction* 65 (2001) 1271-1277; C. M. Markey, E. H. Luque, M. Múnoz de Toro, C. Sonnenschein and A. M. Soto, *Biology of Reproduction*, 65 (2001) 1215-1223; M. Sakaue, S. Ohsako, R. Ishimura, S. Kurosawa, M. Kurohmaru, Y. Hayashi, Y. Aoki, J. Yonemoto and C. Tohyama, Journal of Occupational Health, 43 (2001) 185-190; O. Takahashi, and S. Oishi, Environmental Health Perspectives, 108 (2000) 931-935; Chhanda Gupta, *Proceedings of the Society for Experimental Biology and Medicine*, 224 (2000) 61-68; K. Howdeshell, A. K. Hotchkiss, K. A. Thayer, J. G. Vandenbergh and F. S. vom Saal, *Nature*, 401 (1999) 762-764].

The problem of exposure to BPA has not only remained largely unresolved but BPA continues to be the prime material used in the making of polymers used for consumer products and engineering goods. However, a wide variety of synthetic bis-phenolic compounds other than BPA have also been identified and processes for making polymers using them has been worked out. This has produced a great variety of polycarbonates, copolycarbonates and mixed carbonates without addressing the inherent problem of toxicity and clearly defined biodegradability where the biodegraded products do not overload the ecosystem and sustainability. Examples of such synthetic bisphenolic compounds are many, although most of these resemble 2,2-disubstituted propane, the core structure found in BPA. Such compounds are mentioned in the U.S. Pat. No. 6,562,433 (2003) and U.S. Pat. No. 5,412,061(1995).

Notably, other than PCs made using aromatic bisphenols, aliphatic and nonphenol based polycarbonate, polycarbonate amides and polycarbonate esters are important material that are also manufactured in large quantities, especially for their specific application as biodegradable materials. These are prepared by various processes, e.g., (i) epoxide opening with carbon dioxide [U.S. Pat. No. 3,706,713 (1972); Il Kim , Min Ju Yi, Seung Hoon Byun, Dae Won Park, Bu Ung Kim, Chang Sik Ha, Macromolecular Symposia: Special Issue: Biobased Polymers: Recent Progress, 224 (2005) 181-192; M. M. Dharman, j-Y. Ahn, M-K. Lee, H-L. Shim, K-H. Kim, I-P. Kim, and Dae-Won, Research on Chemical Intermediates, 34 (2008) 835-844]; (ii) interfacial phosgenation, e.g., to give unsaturated polycarbonates [I. A. Kamal, High Performance Polymers, 6 (1994) 149-154]; (iii) melt polycondensation, to prepare poly[(tetramethylene carbonate)-co-(sebacic anhydride)], [X. Congming, and K. J. Zhu, Polymer International, 50 (2001) 414-420]; (iv) ring-opening polymerization, [F. Jun, X-L. Wang, H. Feng, R-X. Zhuo, Macromolecular rapid communications, 28 (2007) 754-758]; (v) solution polycondensations, [M. Yokoe, K. Aoi, M. Okada, Journal of polymer science. Part A. Polymer chemistry, 43 (2005) 3909-3919]; (vi) fabrication of Diblock Methoxy Poly(ethylene glycol)-poly(tetramethylene carbonate), [J. Feng, W. Su, H-f Wang, F-w. Huang, X-z. Zhang and R-x. Zhuo, *ACS Appl. Mater. Interfaces*, 1 (2009) 2729-2737]; (vii) enzymatic Ring-Opening Polymerization [R. Wu, T. F. Al-Azemi and K. S. Bisht, Biomacromolecules, 9 (2008) 2921-2928].

Renewable natural polyphenols, that are known for their benign nature and, in some instances, for their beneficial and nutritional effect on human, can be used to make polycarbonates with desirable properties and fulfill the currently unmet needs of the consumers.

Polyurethanes (PU), another family of thermoplastic polymers of commercial interest, are prepared by well known reaction between a 'diol' and a 'di-isocyanate'. Depending on the nature of the bifunctional unit used, urethane resins can be aliphatic, aromatic or a combination of both. Physical properties of PU polymer which broadly depends on the extent of crystalline and amorphous regions within the polymer ('segmentation') also depends on the monomer used as well as the method and the temperature of the reaction. In general PU is made either by one step process in which two monomers are mixed and allowed to react in the presence of a catalyst, or in two steps, by first making a prepolymer having excess isocyanate (up to 15% by weight) under controlled conditions and then reacting with diols or diamines as chain extender. Introducing a branched trihydroxy or triamine in the mix can provide branched PU. The branching polyol can be part of the mixture in one pot reaction or used first to make a branched prepolymer followed by reaction with a linear polyol or vice versa. However, reaction between symmetrical glycols and symmetrical disocyanates results in the production of high grade, high modulus PU [ref Handbook of polyurethanes, by Michael Szycher, (1999), CRC Press LLC, Florida, USA]. PU has as wide a range of applications similar to PC, being used both in the industrial scale, for consumer products as well as for making medical devices. In many instances, biodegradability and formation of non-toxic residues due to natural wear and tear of the product, has become an important and sometimes critical criterion.

Carefully selected, natural polyphenols can play a distinctive role in the preparation of safe, biodegradable PU polymers suitable for use in several of these, especially in in-vivo, applications. It is possible to choose from di- and tri- (poly-) hydroxyl polyphenols in order to make linear, branched or mixed type PU.

Also, it is noteworthy that biodegradable polymer materials find use in almost all aspects of human life and activities, three most commercially important of which are automotives, medicine, and packaging all of which require environmentally friendly, non-toxic and biocompatible polymers. However the level of biodegradation vis-à-vis to other required properties needs tailoring for each industry in order to create the most appropriate material.

While biodegradability is desirable for all polymeric material, especially for those used under the generic name 'plastic', it is particularly desirable for those polymers that will be used in fabricating certain products for in-vivo applications. Furthermore, it is important to be able to make biodegradable polymers with appropriate properties for specific end uses, e.g., resorbability of the polymeric materials used for sutures and temporary supports and biocompatibility as well as stability in the presence of biofluids of the material used for orthopedic implants. Another important area of application of biodegradable polymers is their use for drug delivery, where the rate of degradation and physical characteristic of the degrading polymer determines the in-vivo availability and the pharmacokinetics of the otherwise entrapped drug substance. Most studied and common polymers used for drug delivery are PGA, PLA and LPLA-co-PGA [Chang-Sik. Ha and J. A. Gardella, Jr., *Chem. Rev.*, 2005, 105 (11), pp 4205-4232; Biodegradable polymers for industrial applications, R. Smith (Ed), CRC Press LLC (2005)]. U.S. Pat. No. 7,365,148, describes the preparation of polycarbonates using Isosorbide, a ether diol prepared from polysaccharides, in combination with other aliphatic diols. Currently, a large number of biodegradable polymers are available, that have been synthesized, found in nature and modified, or, made from chemicals that have been harvested following chemical or enzymatic treatment of natural raw materials. Depending on the evolution of the synthesis process, four different classifications of biodegradable polymers for in-vivo applications have been proposed, (i) polymers from biomass i.e., agro-polymers from agricultural resources (e.g., starch, cellulose); (ii) polymers obtained by microbial production, e.g., the polyhydroxy-alkanoates; (iii) chemically synthesised polymers that are prepared using monomers obtained from agro-resources, e.g., polylactic acid (PLA), polyglycolic acid (PGA); and (iv) polymers whose monomers and polymers are obtained conventionally, by chemical synthesis (monomers may originate from petroleum sources). First three of these above mentioned categories are obtained from renewable resources.

A number of most popular biodegradable polymers for in-vivo applications fall under the category of polyesters along with those that are a combination of polyesters with amides and carbonates. Additionally, novel di- and tri-block polymers, and other synthetic polymers, such as polyorthoester, polyanhydrides, polyhydroxyalkanoate, polypyrroles, poly(ether ester amide)s, fatty acid based polymers, and supramolecular polymers are being used and studied for their use as biomaterials [J. P. Jain, M. Sokolsky, N. Kumar, A. J. Domb, Polymer Reviews, 48 (2008) 156-191; M. Martina, D. W. Hutmacher, Polymer International, 56 (2007) 145-157; R. A. Gross and B. Kalra, Science, 297 (2002) 803-807; W. Amass, A. Amass, and B. Tighe, Polymer International, 47 (1998) 89-144].

Biodegradable polymers made from nutritionally relevant natural polyphenols and their appropriate derivatives are eminently suited for in-vivo applications, e.g., as material to make devices, and as drug delivery vehicles, especially when their degradation products are GRAS designated. It is likely that the polymer properties, e.g., solubility and time to degrade, can be modulated by incorporating different proportions of one or more of the said polyphenol monomers or by introducing other known monomers in the polymerization mixture as well as by the choice of constituent chemical linkages. Such material can be particularly exciting for drug delivery, since the tailored polymers may have one or more types of bonds, chosen, without limiting, from e.g., carbonate, urethane, thioether, carbamate, thiocarbamate, esters. The degradation half lives can be modulated by varying the ratio of chosen linkages.

This invention introduces natural phenolic compounds as renewable and green alternative to the synthetic phenols, and demonstrates that they can be used to make a wide variety of polymers. A number of naturally occurring polyphenolic compounds are well known (Chart 1) and some of these are active ingredients of food and nutritional supplements. Several of these are better known as anti-oxidants and/or free radical scavengers, and may help to maintain good health and reduce incidence of some of the life style related disorders. These compounds possess the characteristic phenolic hydroxyl function and/or reactive hydroxylic groups, thus making them suitable for conversion to polymeric material.

In the current disclosure, curcumin (bis-hydroxy), resveratrol (tris-hydroxy) are two representative, but non-limiting, examples of natural, sustainable polyphenols that have been used as such, and as their derivatives to make polycarbonates (PC), polyurethanes (PU), PC-PU polymers having both PC and PU linkages, mixed polycarbonates, biodegradable polymers having both ester and carbonate linkages. Furthermore, utility of these natural polyphenols have been further extended by the synthesis of their respective allyl functionalized monomers. Allyl and vinyl groups are known to polymerize under radical initiating conditions, and also react with thiols to produce thiol-ether linkages. Allylic groups can be converted to epoxides thereby providing glycidyl ethers and glycidyl esters which are reagents of choice as crosslinkers and as monomers useful in making a variety of polymers as well as modifying them.

Commercially polycarbonate is made by a transesterification reaction where a carbonate diester is condensed with a dihydroxy compound by a process known as 'melt' or 'transesterification' technique. This reaction is performed without a solvent, and is driven to completion by mixing the reactants under reduced pressure and high temperature with simultaneous distillation of the phenol produced by the reaction. This process is preferred over other techniques (e.g., phase transfer, interfacial process) since it does not use phosgene and solvents, has no complicated work up process as well as minimizes the formation of cyclic and low molecular weight oligomers [U.S. Pat. No.: 5,221,761; EP19910116678; U.S. Pat. Nos.: 5,412,061; 6,562,433; 7,148,312]. Laboratory processes for making polycarbonates using Triphosgene and p-Nitrophenyl chloroformate are also known [H. Eckert, and B. Forster, Angew. Chem. Int. Ed. Eng.1 26 (1987) 894; S. Sun, K. Hsu, T. Chang, Polym. J., 29 (1997) 25; Erica H. Martin and William J. Brittain, Polymer Bulletin, 47 (2002) 517-520]. The melt technique, most used industrial process, is preferred to make polycarbonates from CCM, THCCM, RSVR and DHRSVR. The carbonic acid diester which is used in the production of the polycarbonate of the present invention may be, but is not limited to, diphenyl carbonate, dinaphthyl carbonate, bis (diphenyl) carbonate, dimethyl carbonate, diethyl carbonate, dibutyl carbonate or the like. However, diphenyl carbonate (DPC) is preferred from the points of view of reactivity and overall cost.

Usable catalysts are often chosen from a nitrogen-containing basic compound, an alkali metal compound, an alkaline earth metal compound etc., or a combination of two kinds or more. It is preferable to use a combination of nitrogen containing base and alkaline earth metal.

Usually, a diol and a carbonic acid diester, which are raw materials, are subjected to a preliminary reaction by heating them at atmospheric pressure preferably in the presence of a polymerization catalyst into a melt and subsequently the melt is stirred under reduced pressure while being heated (200° C.-higher) to distil the formed phenol. The reaction system is preferably kept in an atmosphere of inert gas such as nitrogen or argon. In the production method of the present invention, it is preferable to suppress the reaction temperature as low as possible in order to prevent the decomposition of the starting material, and obtain a clean product. For this, the polymerization temperature is preferably in the range from about 180° C. to about 280° C., more preferably in the range from about 230° C. to about 260° C.

Mixture of more than one polyphenol from natural sources can be used in the mix to make polycarbonates using the preferred process. Examples are, (a) mixtures of one or more polyphenols selected from CCM, THCCM, RSVR, DHRSVR; (b) one or more chosen from CCM, THCCM, RSVR, DHRSVR and mixed with other commercially available bisphenols; and (c) mixtures of one or more polyphenols selected from CCM, THCCM, RSVR, DHRSVR and mixed with non aromatic diols, preferably chosen from those prepared from renewable sources, e.g., among others, ethane diol, propane diol, butane diol, isosorbide as well as poly (tetramethylene ether) glycol and poly (ethylene ether) glycol). In such mixtures, proportion of bisphenols or other diols that are mixed with the natural polyphenol may vary anywhere between 2-98%.

In all polycarbonate reactions, suitable chain stoppers (0.5 to 10 mol %) can be chosen from, e.g. phenol, p-chlorophenol, p-tert-butylphenol or 2,4,6-tribromophenol, and also long-chain alkylphenols, such as 4-(1,3-tetramethylbutyl)-phenol, in accordance with DE-OS 2842005, or monoalkylphenols or dialkylphenols having a total of 8 to 20 C atoms in the alkyl substituents, in accordance with German Patent Application P 3506472.2, such as 3,5-di-tert-butylphenol, p-iso-octylphenol, p-tert-octylphenol, p-dodecylphenol and 2-(3,5-dimethyl-heptyl)-phenol and 4-(3,5-dimethyl-heptyl)-phenol. One chain stopper is Eugenol—a naturally occurring phenol with allyl substituent, isolated from various natural sources like clove, nutmeg, cinnamon and others.

Further, it is possible to prepare higher molecular weight polycarbonate resin using a solid state polymerization method after the preparation of the first polycarbonate [U.S. Pat. No. 7,148,312]. This and other modified processes can be implemented to prepare high molecular weight polycarbonates from CCM, THCCM, RSVR and DHRSVR and various combinations noted earlier.

As noted before, PU can be prepared by reacting diols with diisocyanates. In one instance this is done in one step where a diol and a diisocyanate are mixed in preferred ratios dissolved in aprotic solvent, e.g., p_dioxane, dichloromethane, tetrahydrofuran, N,N-dimethylformamide, chloroform, and allowed to polymerize in the presence of a base as the activator. Depending upon the proportion of the two monomers used, the final polymer mixture will have either hydroxyl or isocyanate as the reactive end group. The reactive isocyanate end group can be capped, preferably by reacting with an alcohol or amine. Diols, which can also act as 'chain extenders' in the two step process, can be chosen from known aliphatic, araliphatic, aromatic and/or cycloaliphatic compounds, usually, without limiting to, alkanediols of 2-10 carbon length may be preferred. In other cases, the diol can be higher molecular weight compounds, for example polyesterols, polyetherols and/or polycarbonatediols, collectively referred to as "polyols". In the two step process, higher than stoichiometric proportion of the diisocyanate is used to afford a prepolymer with isocyanate end groups (calculated to ensure upto 15% of the weight of the polymer) which is then treated with diol 'chain extender to give the final product.

The catalyst, generally an organic base, is preferably chosen from tertiary amines such as triethylamine, dimethylcyclohexylamine, N-methylmorpholine, N,N'-dimethylpiperazine, 2-(dimethylaminoethoxy)ethanol, diazabicyclo[2,2,2] octane (DABCO).

Preferred isocyanate can be chosen from known aliphatic, cycloaliphatic and/or araliphatic and aromatic compounds, for example trimethylene, tetramethylene, pentamethylene, hexamethylene, heptamethylene and/or octamethylene diisocyanate; 2-methylpentamethylene 1,5-diisocyanate; 2-ethylbutylene 1,4-diisocyanate; pentamethylene 1,5-diisocyanate; butylene 1,4-diisocyanate; 1-isocyanato-3,3,5-trimethyl-5-isocyanatomethylcyclohexane (isophorone diisocyanate, IPDI); 1,4- and/or 1,3-bis(isocyanatomethyl)cyclohexane (HXDI); cyclohexane 1,4-diisocyanate; 1-methylcyclohexane 2,4- and/or -2,6-diisocyanate and/or dicyclohexylmethane 4,4'-, 2,4'- and 2,2'-diisocyanatediphenylmethane (MDI); naphthylene 1,5-diisocyanate (NDI); toluene 2,4- and/or 2,6-diisocyanate (TDI); diphenylmethane diisocyanate; 3,3'-dimethylbiphenyl diisocyanate; 1,2-diphenylethane diisocyanate and/or phenylene diisocyanate. Preferable are toluene 2,4- and/or 2,6-diisocyanate (TDI), hexamethylene diisocyanate and/or IPDI, 4,4'-MDI and hexamethylene diisocyanate.

All possible combinations of methods and reagents can be used to prepare a wide variety of PU from selected polyphenols by those practiced in the art. Polyurethanes were prepared using one pot process by reacting CCM, THCCM, RSVR, mixtures of CCM-THCCM or mixtures of RSVR-THCCM with 4,4'-MDI in N,N-DMF, in the presence of DABCO as the catalyst at room temp.

Thermoplastic Polyurethane (TPUs) are thermoplastic elastomers with application in synthetic leathers, fabric coating material, Spandex fibers, automotive instrument panels, caster wheels, power tools, sporting goods, medical devices, and a variety of extruded film, sheet and profile applications and so on.

TPU is a linear multi-block copolymer consisting of two molecular segments, one generally soft, one generally called hard. The soft and hard segments are made from blocks ending with diol and diisocyanate ending blocks. The molecular weight, ratio and chemical type of the hard and soft segments can be varied. Depending on the choice of segments and the chemical bonds forming each block, resulting TPUs can provide considerable number of physical property combinations, thus providing materials adaptable to dozens of uses. Typically, TPUs are made using commercial diisocyanates, e.g., 4,4'-diphenylmethane diisocyanate (MDI) in conjunction with polyester or polyether diols. Some work has been carried out using polyethercarbonate diols for the synthesis of TPUs [H. Tanaka, and M. Kunimura, Polymer Eng., and Sci., June 2002; R. F. Harris, M. D. Joseph. C. Davidson. C. D. Deporter, and V. A. Davis, J. Appl. Polymer Sci., 41(1990) 487; R. F. Harris, M. D. Joseph, C. Davidson, C. D. Deporter, and V. a. Davis, J. Appl. Polymer Sci, 41 (1990) 509; R. F Harris, M. D. Joseph, C. Davidson, and C. D. Deporter, J. Appl. Polymer Sci., 42 (1991)3241; R. F. Harris, M. D. Joseph, and C. Davidson, J. Appl. Polymer Sci., 46(1992) 1843]

TPUs typically bridge the gap between rubber and plastics, by having materials in grades ranging from soft and flexible to very rigid. It is important to note that some of these also require food-contact regulations and the biocompatibility requirements of FDA.

Natural polyphenols, e.g., CCMN and RSVR, themselves or in combination with other diols, and di-isocyanates, all preferably derived from renewable resources, should provide biocompatible, thermoplastic polymers that are alternatives to the currently available TPU.

A polycarbonate prepolymer of polyphenols having free hydroxyls can be reacted with appropriate diisocyanates in the presence of a catalyst to give urethane linked block-polycarbonate polymer, wherein the prepolymers can be a mix and match of those made from one kind of polyphenol (homo PC), a mixture of polyphenols (hetero PC) or a mixture of natural polyphenols and other diols Polycarbonate prepolymer of polyphenols, e.g., CCM, THCCM, RSVR and DHRSVR, having free hydroxyls can react with diisocyanates to give PU linked block-PC polymer.

Polycarbonate prepolymer of polyphenols, e.g., CCM, THCCM, RSVR and DHRSVR, having free hydroxyls can react with diisocyanates in the presence of other suitable diols and a catalyst to give co-block-polyurethane-polycarbonate block co-polymers, where the diols used can be, e.g., without limiting, alkanediols of 2-10 carbon length, diols of higher molecular weight compounds referred to as "polyols", copolycarbonate diols (coPCDs), e.g., polyhexamethylene carbonate diol (PHMCD).

Polyurethane prepolymer of polyphenols, e.g., CCM, THCCM, RSVR and DHRSVR, having free isocyanates can be reacted with appropriate diols and a catalyst to give TPUs whose property will depend of the type of diol used, e.g., without limiting, alkanediols of 2-10 carbon length, diols of higher molecular weight compounds referred to as "polyols", copolycarbonate diols (coPCDs), e.g., polyhexamethylene carbonate diol (PHMCD) and those prepared using natural polyphenols and other diols as noted earlier.

These and other such combinations can be envisioned to make a variety of polymers, containing natural polyphenols, such as CCM, THCCM, RSVR and DHRSVR.

Further, various function-imparting agents can be optionally added according to the use of all such polymers, e.g., PC, PU, PC-PU, made from polyphenols, such as CCM, THCCM, RSVR and DHRSVR. Such agents are, for example, heat stabilizers, stabilization adjuvants, plasticizers, antioxidants, photostabilizers, nucleating agents, heavy metal-inactivating agents, flame retardants, lubricants, antistatic agents, ultraviolet absorbers etc.

Additionally, depending on the use, the polymers of the present invention can be optionally compounded with various organic or inorganic fillers, fibers etc. The examples of the filler are carbon, talc, montmorillonite, hydrotalcite etc., and the examples of the fiber are various synthetic fibers, glass fibers, quartz fibers, carbon fibers and natural fibers.

Biodegradable polymers made from non-toxic natural polyphenols are suitable substitutes for those material made from controversial bisphenols especially for in-vivo applications. More importantly, biodegradable polymers made from bisphenols are not popular for drug delivery purposes, for which a number of mixed polycarbonates and notably the biodegradable polyesters are well known (FIG. 2). However, all biodegradable polymers need further fine tuning to modulate the rate of degradation that affects the drug delivery and the pharmacokinetics of the released drug.

Biocompatible thermoplastic polycarbonates suitable for medical devices can be made using one or more natural polyphenol, e.g., CCM, THCCM, RSVR or DHRSVR and reacting with a suitable diol, e.g., one chosen from HO—$(C_nH_{2n})$—OH, where n ranges from 2-6; ether diols, e.g., isosorbide; and a carbonic acid diester, e.g., diphenyl carbonate in the presence of polymerization catalysts under melt polymerization conditions.

Accordingly, other biocompatible polymers, such as, polycarbonate-ester, polycarbonate-ether, polyesters, polyesteramides, can also be made using natural polyphenols, such as CCM, RSVR and their respective hydrogenated products THCCM and DHRSVR Additionally, biodegradable polymers for drug delivery can be made using suitable derivatives of polyphenols whereby new functionalities are introduced on to the natural polyphenol template. Newly introduced functions such as, but not limited to, carboxy, amino, allyl, vinyl, sulfonyl, epoxide, provide options to make newer varieties of polymers, used as crosslinkers during polymerization or to modify existing polymers.

A polyphenol or a mixture of polyphenols can be selectively or exhaustively derivatized to their respective allyl derivatives, mixed with di- oligo-thiolated monomers, oligomers or polymers, preferably in a aprotic solvent and reacted either by UV irradiation or by heating in the presence of a suitable initiator to give new polymers, preferably biodegradable polymers.

Allyl derivatives of CCM, RSVR, THCCM and DHRSVR are some such compounds with a variety of subsequent uses including their application as monomers. Per O-allylated, selectively O-allylated and tetra- allyl derivatives of CCM and THCCM namely, (E,E)-1, 7-Bis(4-O-allyloxy carbonyl-3-methoxy phenyl)-4,4(gem-di-C-allyl)-1,6-heptadiene-3,5-dione and 1,7-Bis(4-O-allyloxy carbonyl-3-methoxyphenyl)-4,4(gem-di-C-allyl)-heptane-3,5-dione, all suitable and novel monomer substrates, could be prepared.

It is noteworthy that manipulations of the allylic function can provide intermediates suitable for further polymerizations as well as afford crosslinkers to modify suitable polymer substrates, e.g., di- and tri-glycidyl ethers could be prepared from the corresponding di- and tri-O-allyl derivatives of THCCM and DH resveratrol by epoxidation of the allylic double bond, using m-chloro perbenzoic acid (MCPBA) from among known reagents and methods [Robert W. Murray and Megh Singh, Organic Syntheses, Coll. Vol. 9 (1998) 288; 74 (1997) 91; Tsutomu Katsuki, K. Barry Sharpless, J. Am. Chem. Soc., 102 (1980) 5974-5976; Eunsook Ma and Jongwon Kim, Molecules, 8 (2003) 886-893; Elizabeth Golan, Aviv Hagooly and Shlomo Rozen, Tetrahedron Lett., 45 (2004) 3397-3399; Olga Bortolini, Giancarlo Fantin, Marco Fogagnolo, Synthesis (2009) 1123-1126]. Glycidyl ether derivatives of bisphenols are well known for preparing resins [USPTO: 20090029058; IPC8 Class: AC08L6300FI -USPC Class: 525523; R. Mustafa, M. B. Haft Othman, H. Ismail and Z. Ahmad, Malaysian Polymer Journal, 4 (2009) 68-75; D. Bogdal, J. Pielichowski, P. Penczek, J. Gorczyk, a Kowalski, Polymery, 47 (2002) 11-12]. Such epoxides are useful in making epoxy resins and can be further mixed and matched to provide epoxy resin compositions with newer physicochemical properties [U.S. Pat. Nos. 5,160,783; 5,753,726; 5,969,060; 5,969,060; 7,354,978; IPC8 Class: AC08L6300FI/USPC Class: 525523; US 2010/0104794 A1].

Allylic groups in the allyl ether and allyl carbonate derivatives can undergo polymerization under a number of conditions [U.S. Pat. Nos. 4,686,266; 3,966,840; 5,312,871, 4,326,049; Norman G. Gaylord, J. Polym. Sci., 22 (1956) 71-78; A. Matsumoto, N. Kawasaki, and T. Shimatani, Macromolecules, 33 (2000) 1646 -1650; A. Matsumoto and H. Aota, Designed Monomers & Polymers, 7 (2004) 687-699; C. Heydel, P. Cassagnau, and A. Michel, J. Rheology, 43 (1999) 499-519; T. Y. Lee, Z. Smith, S. K. Reddy, N. B. Kramer and C. N. Bowman, *Macromolecules,* 40 (2007) 1466 -1472]

Whereas such polymerization can be carried out with allyl ether and allyl carbonate derivatives of polyphenols, e.g., those made from CCM, RSVR, THCCM and DHRSVR, using them individually and in admixture with other allylated or vinyated mono-, oligo- or polymeric material, Allyl ethers of CCM, RSVR, THCCM and DHRSVR are preferably polymerized by reacting with di- and higher thiol substituted monomers under free radical conditions using preferred free radical initiator, azo-bis-isobutyronitrile (AIBN) or by UV radiation. Free radical and UV initiated reactions of allyl and vinyl groups is well known. [U.S. Pat. Nos. 4,326,049; 6,605,691; 7,009,025; 7,288,608; U.S. Patent application number: 20100063209; Andrew B. Lowe, Polym. Chem., 2010, 1, 17-36; A. S. Goldmann, A. Walther,. L. Nebhani, Raymond Joso, D. Ernst, K Loos, C. Barner-Kowollik, L. Barner, and A. H. E. Müller, Macromolecules, 42 (2009) 3707-3714; C. Rim, L. J. Lahey, V. G. Patel, H. Zhang and D. Y. Son, Tetrahedron Letters, 50 (2009) 745-747; L. A. Connal, C. R. Kinnane, A. N. Zelikin and F. Caruso, Chem. Mater., 21 (2009) 576-578; R. A. Ortiz, A. E. Garcia Valdéz, M. G. Martinez Aguilar and M. L. Berlanga Duarte, Carbohydrate Polymers, 78 (2009) 282-286; V. S. Khire, A. M. Kloxin, C. L. Couch, K. S. Anseth, C. N. Bowman, J. Polym. Sci.:Part A: Polymer Chem., 46 (2008) 6896-6906: A. E. Rydholm, S. K. Reddy, K. S. Anseth and C. N. Bowman, Polymer, 18 (2007) 4589-4600D; Burget, C. Mallein and J. P. Fouassier, Polymer, 45 (2004) 6561-6567; C. R. Morgan, F. Magnotta, A. D. Ketley, J. Polym. Sc.: Polymer Chem., Edition, 15 (on line 8 April 2003) 627-645; A. A. Avetisyan, F. P. Sidelkovskaya and R. M. Ispiryan, Russian Chemical Bulletin, 13 (1964) 1206-1210]

Noted and included, chemical modification of inherent functional groups, i.e., carbonyl and hydroxyls, reactive methylene, unsaturated bonds in CCM, RSVR, THCCM and DHRSVR and their allyl derivatives, before polymerization or after polymerization, offer opportunities to make polymers with newer physicochemical properties, crosslinked and crosslinkable polymers (between its own polymer chains and/or with other crosslinkable polymers).

Blended Polymers: Polycarbonates made from Polyphenols can be blended with other material to give polymer blends with improved and desirable properties. Methods for making polycarbonate blends have been documented (WO 2008028695 20080313; USPTO Application #: 20090142537; application Ser. No. 11/427,472 issued Jun. 30, 2009; U.S. Pat. No.: 7,235,598 Publication Date: Jun. 26, 2007). Making PC-PU: Patent US2008146766(A1); PC-Polyorganosiloxane: WO/2008/142109; Polycarbonate-Poly(ester-ether) copolymer composition: WO/2009/036229, (Priority Dates: 60/971,768 12 Sep. 2007 US and Ser. No. 11/961,692 20 Dec. 2007 US)Aromatic polycarbonate resin composition: U.S. Pat. No. 6,355,767—Issued Mar. 12, 2002.

Polycarbonate resin composition: polycarbonate-polyorganosiloxane copolymer, (WO/2009/075232)/PCT/JP2008/072170

The polymers of the present invention are suitable for use as molded materials, coating materials for metal and non-metal to sheets to be used in packing of food, pharmaceuticals and cosmetics, as biocompatible coating materials for devices (medical and other like packaging material), antioxidant polymeric material as ingredients in formulations for personal care products, nutraceuticals, cosmaceuticals, as excipients in drug formulations and for drug delivery purposes. Due to their well documented antioxidant property and recent findings about their possible applications in maintaining good health, Curcumin, Resveratrol, Tetrahydrocurcumin and Dihydroresveratrol, as polymeric materials, can have wide applications under both in-vitro and in-vivo conditions. In such instances where the thiol is biocompatible, e.g., PEG-dithiol, and the natural polyphenol is one of well known GRAS designated compounds, e.g., antioxidants like resveratrol, curcumin, lutein, epigallocatechin, tea polyphenols, the final product could be a composition that is suitable as a nutritional supplement with a range of solubility and biodegradability characteristics.

Appropriate mixtures of the curcumin containing polymers and other commercially available polymers should provide new, currently unknown, blended polymer mixtures (with new applications). When such polycarbonates or their blended variety have good heat resistance, they can have various uses including optical parts such as optical sheets, optical disks, information disks, and optical lenses and prisms, various machine parts, building materials, car components, and various resin trays and dishes. Polycarbonates of the present invention can be mixed with a bio-based polymer, other synthetic resin, various other polymers, for example, an aromatic polyester, a polyamide, polystyrene, polyolefin, polyacrylic acid, polyurethane, polylactic acid and aliphatic polyester.

By virtue of biodegradability, the polycarbonates and the thioether-ester-carbonate linked polymers of the present invention can be used as films and sheets for packaging, films and sheets for uses including food wrapping, general packaging, compost bags etc., for the delivery of nutraceuticals and therapeutic agents.

It will be appreciated by those skilled in the art that various omissions, additions and modifications can be made to the invention described above without departing from the scope of the invention, and all such modifications and changes are intended to fall within the scope of the invention, as defined by the appended claims.

Embodiments

One major embodiment of the present invention is to make polymers from relevant phenolic compounds that can be obtained from natural sources thus providing alternative polymeric material that are safer to the consumer and less burdensome to the environment by being biocompatible, biodegradable and non-toxic.

A second embodiment is to make suitable 'derivatives' of natural phenols, e.g., allyl derivatives of the phenols, and use them as such and in combination with appropriate commercially available 'building block' monomers to make copolymers.

The third embodiment is to use existing, already established and popular industrial processes to make copolymers by combining one or more of natural polyphenols with other commercially known, well accepted compounds (monomers) thus providing newer, natural polyphenol embedded, biodegradable and safer copolymers.

A fourth embodiment is to firstly, make block copolymers by combining two types of oligomers made from structurally different natural polyphenols to give block copolymers of more than one type of polyphenol; secondly, making polymers from a mixture of prepolymers made from natural polyphenols and that made from commercially well known monomers, thus providing newer varieties of block copolymers, incorporating natural polyphenols, having choice of linkages that are biodegradable, biostable or both.

A fifth embodiment of the invention is to prepare mono- and oligo-substituted derivatives of natural polyphenols for their subsequent use in making polymers different from the ones made by using them in their natural form.

A sixth embodiment is to make biodegradable polymers specifically effective for drug delivery and for coating purposes.

A seventh embodiment is to use the new polymers, the mixed polymers and polymer resins for ex-vivo engineering applications, e.g., and not limited to, molded products, sheets etc.

An eighth embodiment is to use the new biocompatible polymers as excipients, for drug delivery, coating of medical devices as well as in formulations for use in personal care and healthcare products.

Other embodiments of the invention also include:

1. Synthesis of polymers, such as, without limiting, homopolymers, co-polymers, block polymers, block co-polymers, grafted polymer, 3D polymer, interpenetrating polymer, having chemical linkages, such as (without limiting), carbonates, ethers, carbamates (urethanes), thiocarbamate, thioethers, esters and a combination of one or more of such chemical linkages, using naturally occurring plant polyphenols.

2. Synthesis of derivatives of the same polyphenols as the ones used under objective 1 to give suitable monomers for the purpose of their subsequent polymerization to give newer varieties of polymers.

3. More specifically, synthesis of polycarbonate and mixed polycarbonate ('copolycarbonates') polymers using one or more of the following polyphenols, namely, Curcumin [CCM, also known as Diferuloyl methane and chemical name (E,E)-1,7-Bis(4-hydroxy-3-methoxy phenyl)-1,6-heptadiene-3,5-dione]; hydrogenated curcumins, i.e., Tetrahydrocurcumin (THCCM); Resveratrol (RSVR), chemical name: 3,5, 4'-trihydroxy-trans-stilbene (3,5,4'-THS); hydrogenated Resveratrol [DH-Resveratrol, chemical name: 1-(3',5'-dihydroxy phenyl)-2-(4"-hydroxy phenyl)-ethane]; using them individually, as mixtures and in admixture with other commercially available bis-phenols, e.g. (not limiting to), 2,2-bis-(4-hydroxyphenyl)propane, commonly known as Bisphenol A or BPA.

4. Furthermore, synthesis of polyurethanes from the polyphenols in embodiment 3, individually, as mixtures of one or more of the said polyphenols or in admixture with other commercially available monomers and a relevant di-isocyanate or a di-isothiocyanate in the presence of a suitable catalyst.

5. Additionally, synthesis of block polymers having both carbonate and urethane linkages utilizing one or more polyphenols mentioned under embodiment 3, by first preparing oligocarbonates of one polyphenol or a mixture of more than one, and reacting such oligomeric blocks having phenolic end functions with selected di-isocynates in the presence of a suitable catalyst.

6. Accordingly, in reference to objective 5, synthesis of block co-polymers, when oligomeric blocks (prepolymers) are made using polyphenols, selected from those in embodiment 3 and those available commercially where the blocks are either copolymers made from a mixture of polyphenols or prepared as homogenous polymer blocks made from any one polyphenolic material followed by mixing the prepolymer blocks in predetermined ratios for the final polymerization via the same or a second type of chemical linkage giving high molecular weight material.

7. More specifically, synthesis of polymers as described in embodiment 6, when the first block of polymers are polycarbonates of CCM and THCCM having phenolic end groups, which are then linked via urethane linkages using 4,4'-Methylene diphenyl diisocyanate (MDI) to give final block polymers having homopolycarbonate blocks, co-polycarbonate blocks or both, linked via di-isocyanate linking agents to give urethane linked block polycarbonate/copolycarbonate polymers.

8. Additionally, synthesis of polymers as described under embodiment 6, when the first block polymers are polyurethanes having phenolic end groups that are then linked via carbonate links using phosgene, phosgene equivalent reagents or bis-chloroformate linkers.

9. Making thermoplastic polymers by reacting polycarbonate prepolymer of polyphenols, e.g., CCM, THCCM, RSVR and DHRSVR, having free hydroxyls with diisocyanates in the presence of other suitable diols and a catalyst to give co-block-polyurethane -polycarbonate block co-polymers, where the other diols used can be, e.g., without limiting, alkanediols of 2-10 carbon length, diols of higher molecular weight compounds referred to as "polyols", copolycarbonate diols (coPCDs), e.g., polyhexamethylene carbonate diol (PHMCD).

10. Making thermoplastic polymers by reacting polyurethane prepolymer of polyphenols, e.g., CCM, THCCM, RSVR and DHRSVR, having free isocyanates with appropriate diols and a catalyst where the diol used are, e.g.,without limiting, alkanediols of 2-10 carbon length, diols of higher molecular weight compounds referred to as "polyols", copolycarbonate diols (coPCDs), e.g., polyhexamethylene carbonate diol (PHMCD).

11. Processes for the synthesis of per-O-alkylated derivatives of natural polyphenols 12. More specifically, first time synthesis of per-O-allyl derivatives of CCM, THCCM, Resveratrol and DH-Resveratrol, including tetra- allyl derivatives of CCM and THCCM namely, (E,E)-1, 7-Bis (4-O-allyloxy carbonyl-3-methoxy phenyl)-4,4 (gem-di-C-allyl)-1,6-heptadiene-3,5-dione and 1,7-Bis(4-O-allyloxy carbonyl-3-methoxyphenyl)-4,4(gem-di-C-allyl)-heptane-3,5-dione.

13. Process for the synthesis of functionalized carbonate derivatives of polyphenols as monomers, for their further use to make polymers, by their reaction with appropriate chloroformate reagents.

14. More specifically, synthesis of di- allyl carbonate derivatives of CCM, THCCM, and tri- allyl carbonate derivatives of Resveratrol and DH-Resveratrol.

15. A process for making linear, 3D, network and other polymers by reacting allyl ether and allyl carbonate derivatives of polyphenols with di- and oligo- thiol monomers using suitable methods, e.g., photoactivation or radical induced polymerization that typically occurs via reaction between the 'ene' component of the allylic group and thiol functions.

16. More specifically, reactions of allyl carbonate derivatives of CCM, THCCM and Resveratrol with pentaerythritol 3-mercaptoacetate (PETMA) to give polymers having carbonate, thiol ether and ester, all three linkages.

17. Preparation of novel mixed polymers with modified properties by suitably combining polymers described in embodiments 3-8 with other physicochemically compatible polymers and doing so in the form of melts.

18. Use of polymers, made in embodiments 3-8, in making moulded products (e.g., containers for storing and using food materials and bottles for adults, children and babies), coating of food containers, for making coated medical devices and as material for manufacturing medical devices for in-vivo applications.

19. Use of polymers in embodiments 3 -8, 15 and 16 as excipients in formulations with other active agents in drug formulations, coating of tablets, for drug delivery and for applications in various food, nutraceutical, cosmeceutical formulations.

20. Use of appropriate oligo- and polymer compositions made in embodiments 15 and 16 made from nutraceutically relevant polyphenols as compositions for delivering the starting polyphenol.

21. More specifically, when such compositions under embodiment 19, are prepared using CCM and RSVR.

22. Use of compositions listed under embodiment 19, irrespective of their solubility characteristics.

23. Use of allyl carbonate and allyl ether derivatives to prepare epoxides useful for making epoxy resins, for crosslinking and for making coated surface.

24. More specifically, a process for making epoxide from the allyl ether derivatives of THCCM and DHRSVR.

25. Use of all inherently fluorescent polymers made in the above claims, more specifically, polymers having CCMN as one of the components, for specific and/or special applications in coated materials, medical devices and consumer products.

26. Use of the allyl carbonate and allyl ether derivatives for making thiol ether linked coating, linear & crosslinked polymers, in applications such as, drug delivery, and coated devices.

EXAMPLES

Materials. All reagents were used without further purification. Curcumin (95%), Diphenyl carbonate (99%), 4-Dimethylaminopyridine (DMAP, 99%) and Bisphenol A (97+%) were purchased from Alfa Aesar. Allyl chloroformate (97%), calcium carbonate ($CaCO_3$, 99+%), 2,2'-azobisisobutyronitrile (AIBN), pentaerythritol tetrakis 2-mercaptoacetate (PETMA), 4,4'-diisocyanatediphenylmethane (MDI), diazabicyclo[2,2,2]octane (DABCO) and pyridine were purchased from Aldrich and Alfa Aesar. Solvents were ACS grade. All liquid reagents and solvents used for reactions were stored over dry molecular sieve 4A. Analytically pure tetrahydrocurcumin (THCCM), dihydro-resveratrol (DHRSVR) were prepared by hydrogenation of the natural precursors dissolved in appropriate solvent, with hydrogen in the presence of 5% Pd on C.

Polyphenols mentioned below shall mean natural Curcumin and Resveratrol as well as their respective Tetrahydro and Dihydro derivatives, i.e., their corresponding hydrogenated versions.

Analyses. Gel permeation chromatography (GPC), to determine molecular weights, was carried out using styragel column (4E, 2, 0.5), as a solution of the carbonates in dichloromethane (4 mg/mL) and an injection volume 100 microliters [at Polymathic Analytical Labs, 3737 Industrial Blvd., Orangeburg, S.C. 29118]. NMR of the $CDCl_3$ soluble polymers were run on a Bruker DRX500 (at NMR facility, Montana State University, Bozeman, Mont.).

Methods. In order that those skilled in the art will be better able to practice the present invention, the following methods and examples are given by way of illustration and not by way of limitation.

Preparation of Alkyl/Aryl -O-Carbonates of Polyphenols

Weighed quantity of polyphenol is dissolved in a previously dried, suitable aprotic solvent, e.g., Chloroform, Dichloromethane, N,N-Dimethylformamide (N,N-DMF), p-Dioxane, Tetrahydrofuran (THF), among others, in the presence of more than equimolar (w.r.t. hydroxylic functions) proportions of a base [triethylamine, Pyridine, or other (excess, usually 3-5 molar excess per hydroxyl function)], maintained between −20° C. to r.t. (20-25° C.), preferably −10 to 5° C., and requisite quantity of Alkyl/Aryl_chloroformate (at least 1.1 molar/hydroxyl group) is added into the stirred solution of polyphenol while maintaining the temperature. Reaction is continued, checked for progress by tlc until completion, i.e., when no starting material is visible. In some cases the temperature is allowed to rise to r.t. for the reaction to come to completion. Adequate quantity of methanol (ACS grade) is added and stirred (1-2 h) to destroy any excess reagent.

On completion, the reaction mixture is diluted with chloroform, (filtered if necessary), the organic solution is washed successively with water, cold aqueous HCL (1N), water, cold aqueous sodium bicarbonate, and finally with water and dried (anhyd. $MgSO_4$). Filtration and evaporation of the organic solution afforded the corresponding carbonate derivative of the starting polyphenol in >90% yield. When necessary, a quick column chromatography gave the pure final product.

Preparation of Alkyl/Aryl-O-Ethers of Polyphenols

Method 1. A solution of polyphenol in chloroform or dichloromethane (sometimes requiring addition of N,N-DMF) containing Alkyl/Aryl halide (generally 2-10 molar excess w.r.t. each hydroxyl) is refluxed in presence of aqueous KOH (0.1-5.0N preferably 0.1-1N) containing catalytic quantity of PTC, e.g., $BU_4N^+I^-$, until tlc of the organic layer indicated absence of starting material and one or more products. The reaction is usually continued to maximize one product. Organic layer is separated, washed successively with aqueous acid (1N HCl, or 5% acetic acid), water, aqueous $NaHCO_3$ (Satd.), and finally with water and dried over anhydrous $MgSO_4$. Filtration and evaporation of the filtrate afforded the corresponding ether derivatives which are purified by column chromatography to give the final product(s).

Method 2. Between 2-10 molar excess (w.r.t. each hydroxyl) of powdered inorganic base (e.g., $K_2CO_3$, $Cs_2CO_3$, or other) is dispersed into a solution of the target polyphenol in an aprotic solvent, usually, N,N-DMF (sometimes mixed with up to 50% Dichloromethane), containing Alkyl/Aryl halide (1.1-3.0 molar excess w.r.t. each hydroxyl) and the slurry allowed to stir at r.t. until the supernatant indicated no starting material. The mixture is diluted with chloroform, filtered under suction through a pad of celite, filtrate washed successively with water, aqueous $NaHCO_3$ (Satd.), and finally with water and dried over anhydrous $MgSO_4$. Filtration and evaporation of the filtrate gave the expected ether derivatives which can be purified by column chromatography to give the final product(s).

Preparation Polycarbonates (PC) of Polyphenols

Polyphenolic compound and Diphenyl carbonate, DPC (1:1-1.5 molar proportion in the case of bisphenols), and catalytic quantities of $CaCO_3$ (5-8 mg) and DMAP (5-8 mg) are weighed into a $N_2$ purged, round bottomed distillation flask containing a stir bar and fitted with a short path vacuum distillation still. The mixture is heated at about 215-220° C. (oil bath) until a melt formed. The flask is gently evacuated (final pressure $10^{-2}$ to $10^{-3}$ Torr), temperature (of the bath) increased to 250→330° C. and reaction continued until distillation of phenol stopped. The flask is cooled to RT (23° C.), and the vacuum released. Generally, a clear liquid forms, which solidifies on cooling down to RT. Products are broken up into smaller fragments and powdered.

Preparation of Polyurethanes (PU) of Polyphenols

Appropriate quantities of the polyphenol and a di-isocyanate [e.g., 4,4'-methylene-bis-(phenyl isocyanate), MDI] are added to aprotic solvent (single or a mixture of more than one solvent, e.g., usually chosen from N,N-DMF, $CH_2Cl_2$, p-Dioxane, Tetrahydrofuran) in a flask to give a clear solution, to which is added catalytic quantity of a base, e.g., DABCO (Diazabicyclooctane), and the reaction mixture is stirred for several hours (2-12 h). Usually a gelatinous mass forms which is broken up, transferred into methanol or ethanol and stirred vigorously at r.t. (2-12 h). The solid is separated from the supernatant, usually by decantation and stirred a second time with the same solvent (4-12 h). Filtration, washing with more solvent under suction and drying under vacuum gives the target product.

Preparation of Mixed PC-PU of Polyphenols

Polycarbonate is first prepared from one polyphenol or from more than one in admixture, following the procedure mentioned above using DPC (between 0.1-1.0 molar, the ratio determines the polydispersity and the size of the oligo-/polymers). The resulting material, a poly-disperse mixture, is dissolved in N,N-DMF to which, MDI (0.5-1.0 molar w.r.t. starting polyphenol/usually in excess of available phenolic hydroxyls calculated based on polydispersity of the PC prepared) and DABCO (Catalytic) are added. The resulting solution is stirred at r.t. (2-12 h) to give a gelatinous to semi-solid mass. Ethanol (dry) is added, the material broken up and the slurry stirred vigorously at r.t. (2-8 h). Filtration under suction afforded a solid that was dried under vacuum to give the final product.

Radical Initiated Polymers: Reaction Between Polyphenol Allyl Carbonates and Mono-, Bis-, Tris- or Tetrakis-Thiols Appropriate quantity of the thiol (e.g., PETMA) dissolved in an aprotic solvent, e.g., p-dioxane, is transferred in a $N_2$ purged flask. AIBN (catalytic) is added and the flask, fitted with a reflux condenser, is warmed (70° C. oil bath) while the content is stirred (15-20 min). Requisite quantity of allyl carbonate compound is added as a solution, preferably in the same solvent in which the thiol is dissolved, e.g., p-dioxane, and the bath temperature raised (90-105° C.). After 2-8 h, the flask is cooled, the content (broken up if it is a gel or a solid mass) is transferred into vigorously stirred cold methanol (1 h). Usually a solid separates which is transferred into fresh methanol, triturated and washed again with fresh methanol (3-4 h), before filtering under suction and drying (vacuum desiccator) to give the final product.

Example 1

(E,E)-1,7-Bis(4-O-allyloxy carbonyl-3-methoxy phenyl)-1,6-heptadiene-3,5-dione (1, Curcumin diallyl carbonate).

Curcumin, CCMN (6.5 g, 17.6 mmol) is dissolved in N,N-DMF (60 mL) and stirred at r.t. (23° C.) over molecular sieve 4A (40 min-1 h). The stirred solution is cooled (0-5° C.) and a solution of allyl chloroformate (4.6 mL, 43.4 mmol) in N,N-DMF (5 mL) was dropped into it over 20-30 min. After the usual work up, the chloroform solution on evaporation gave a crude solid which was recrystallized from ethyl acetate-hexane to give pure 1 (5.88 g, $R_f$ 0.125 in Hexane-Ethyl acetate-Methanol 4:1:0.1 v/v; yield 62%). More 1 could be isolated from the mother liquor.

$^1$H-NMR (ppm, CDCl$_3$). 7.6 (d, 2p); 7.15-7.11 (6p, aromatic); 6.55 (d, 2p); 6.25-5.94 (m, 2p, CH=); 5.85 (s, enol H); 5.45-5.29 (4q, 4p, =CH$_2$); 4.76-4.72 (2t, 4p,allylic OCH$_2$—); 3.89 (s, 6p, OCH$_3$).

Example 2

1,7-Bis(4-O-allyloxy carbonyl-3-methoxyphenyl)-heptane-3,5-dione (2). Tetrahydrocurcumin, THCCMN (1.0 g, 2.68 mmol) is dissolved in a solution of dichloromethane (DCM, 8 mL) admixed with pyridine (1.5 mL) and stirred at 0-5° C. over molecular sieve 4A (30min). A solution of allyl chloroformate (0.85 mL, 8.01 mmol) in DCM (1.0 mL) was dropped into it over 20-30 min while continuing the stirring. TLC (Hexane-ethyl acetate 1:1 and 2:1) after 30 min showed no starting material, one major and a minor product. Ethanol (1.0 mL) was added, stirred (30 min) and the reaction mixture filtered under suction through a bed of Celite. The organic solution was washed with cold aqueous HCl (1N), water, aqueous sodium bicarbonate, dried (MgSO$_4$), filtered and evaporated to give a syrup. Column chromatography using pre-packed silica column (80 g) and eluting with Hexane-Ethyl acetate (1:1, 70 mL and 7:2 gave first the minor product followed by 2, the major product.

$^1$H-NMR, 2 (ppm, CDCl$_3$). 7.0 (d, 2p, aromatic); 6.8-6.7 (m, 4p, aromatic); 5.98 (m, 2p, —CH=); 5.42 (s, enolic CH); 5.43-5.27 (2d, 4p, =CH$_2$); 4.7 (d, 4p, allylic —OCH$_2$—); 3.8 (s, 6p, OCH$_3$); 2.9 (t, 4p, CH$_2$); 2.55 (t, 4p, CH$_2$).

Minor product (3). Ratios of aromatic and allylic signals indicate tri-allyl carbonate product, most likely due to reaction of enolic hydroxyl with allyl chloroformate.

$^1$H-NMR, (ppm, CDCl3). 7.0 (d, 2p, aromatic); 6.21 (s, enolic CH); 5.98 (m, 3p, —CH=); 5.45-5.28 (4broad s, 6p, =CH$_2$); 4.75-4.65 (2d, 6p, allylic —OCH$_2$—); 3.8 (6p, OCH$_3$); 2.9 (t, 4p, CH$_2$); 2.55 (t, 4p, CH$_2$).

Example 3

3, 5, 4'-Tris(O-allyloxy carbonyl)-trans-stilbene (Resveratrol triallyl carbonate, RTAC, 4). Resveratrol (RSVRTRL, 1.15 g, 5 mM) was dissolved in a solution of DCM (3.0 mL) and pyridine (3.5 mL) containing molecular sieve 4A (1.8 g) and stirred at r.t. (1-2 h). The solution is cooled (−20° C.) and a solution of allyl chloroformate (1.8 mL, 16.98 mM) in DCM (2.2 mL) was added dropwise into the cooled stirred solution within 10-20 min. The temperature is slowly raised to 5-10° C. (30 min) when TLC (hexane-ethyl acetate-methanol 3:1: 0.1 v/v) indicated complete conversion to one major product along with a few minor side products. Methanol (1.5 mL) was added and the mixture stirred (at 0-5° C., 1 h) to terminate the reaction. Chloroform (8 mL) was added and the mixture filtered under vacuum. The filtrate was washed successively with cold aq. HCl (1N), water, aq. NaHCO$_3$ and dried (anhyd. MgSO$_4$). Filtration, evaporation of the filtrate and column chromatography of the resulting syrupy crude product (using prepacked silica column, 80 g and hexane-ethyl acetate-methanol 15:1:0.1 v/v as eluant) gave pure 4 (2.39 g, 98.8%).

$^1$H-NMR, 4 (ppm, CDCl$_3$). 7.48 (d, 2p); 7.21 (d, 2p); 7.17 (d, 2p); 7.01 (q, 2p); 6.99 (t, 1p); 5.99 (m. 3p, —CH=); 5.47-5.30 (4m, 6p, =CH$_2$); 4.73 (d, 6p, allylic OCH$_2$—).

Example 4

(E,E)-1- (4-O-allyl -3-methoxy phenyl)-7-(4-hydroxy-3-methoxy phenyl)-1,6-heptadiene-3,5-dione (5, Mono-O-allyl curcumin). Allylation of curcumin (0.74 g) by method 1, using allyl bromide (3.5 mL), TBAI (27 mg), gave compound 5 as a foam after chromatographic purification.

$^1$H-NMR, 5 (ppm, CDCl$_3$). 7.58 (dd, 2p, ethylene protons); 7.14-7.0 (m, 4p, arom); 6.94-6.82 (dd, 2p, arom); 6.51-6.43 (2d, 2p, ethylene protons); 6.11-6.01 (m, 1p, allylic-CH—); 5.86 (bs, D$_2$O exchangeable, Ph—OH); 5.79 (s, 1p, —CH=C(OH)—, 4H of enolate); 5.44-5.27 (2ds with fine splits, 2p, =CH$_2$ of allyl); 4.65 (—OCH$_2$— of allyl); 3.93 (d, 6p, OCH$_3$).

Example 5

(E,E)-1,7-Bis(4-O-allyl-3-methoxy phenyl)-1,6-heptadiene-4,4-di-C-allyl-3,5-dione (6, Tetra-allyl curcumin). Allylation of curcumin (0.27 g) by method 2 at r.t. (13 h), using Cs$_2$CO$_3$ (1 g) and allyl bromide (0.5 mL) in N,N-DMF (3.5 mL) gave 6 as the major product ($R_f$ 0.42, hexane-ethyl acetate 2:1 v/v) which was isolated after work up and column chromatography.

$^1$H-NMR, 6 (ppm, CDCl$_3$). 7.7-7.63 (d, 2p, ethylene protons); 7.08 (dd, 2p, H-6,6', arom); 6.98 (d, 2p, H-2, 2', arom); 6.81 (d, 2p, H-5, 5', arom); 6.64 (d, 2p, ethylene protons); 6.04 (m, 2p, allylic CH— of —O—CH$_2$—CH=CH$_2$); 5.53 (m, 2p, allylic CH— of 4C—CH$_2$—CH=CH$_2$); 5.41-5.26 (2 set of dds, 4p, =CH$_2$ of O—CH$_2$—CH=CH$_2$); 5.12-5.04 (dd & s, 4p, —OCH$_2$— of O-allyl); 4.61 (d, 4p, =CH$_2$ of 4C—CH$_2$—CH=CH$_2$); 3.86 (s, 6p, OCH$_3$); 2.79 (d, 4p, 4C—CH$_2$— of 4C—CH$_2$—CH=CH$_2$).

Example 6

1,7-Bis(4-O-allyl-3-methoxy phenyl)-heptane-3,5-dione (7, Di-allyl Tetrahydrocurcumin), and 1,7-Bis (4-O-allyl-3-methoxy phenyl)-heptane-4,4-di-C-allyl-3,5-dione (8, Tetra-allyl Tetrahydrocurcumin). Allylation of Tetrahydrocurcumin (0.2 g, 0.54 mM) by method 2 at r.t. (4 h), using Cs$_2$CO$_3$ (1 g) and allyl bromide (0.28 mL, 3.2 mM) in N,N-DMF (3.5 mL) gave 7 and 8 and no starting material (TLC, Hexane-Ethyl acetate 2:1 v/v). Prolonging the reaction afforded mostly compound 8. Reaction by method 1, using THCCMN (0.2 g) in chloroform (10 mL), aq. 0.5N KOH (8 mL) and allyl bromide (0.464 mL) produced compound 7 as the major product along with a minor quantity of 8. Pure products were isolated after work up and column chromatography.

¹H-NMR, 7 (ppm, CDCl₃)._6.78-6.62 (6p, arom); 6.05 (m, 2p, —CH= of allyl); 5.4-5.22 2d with splits, 4p, =CH₂ of allyl); 4.56 (bs with splits, 4p, —OCH₂ of allyl); 3.84 (d, 6p, OCH₃). Ratio of aromatic protons to allylic protons: Calc.6:10, found, 6:10.

¹H-NMR, 8 (ppm, CDCl₃)._6.75-6.55 (6p, arom), 6.04 (m, 2p, —CH= of O-allyl); 5.44-5.22 (2d on top of a multiplet, 6p, —CH= of 4C-allyl and =CH₂ of O-allyl); 5.07-5.0 (1s and 1d, 4p, =CH₂ of 4C-allyl); 4.52 (d, 4p, —OCH₂ of O-allyl); 3.82 (s, 6p, OCH₃); 2.74-2.48 (2t at 2.72and 2.52 integrating for 4p each, due to CH₂s at C-1,2,6,7 positions, and 1d at 2.62 integrating for 4p due to 2XCH₂ of 4C-allyl). Total protons, Calc. 40, found by integration: 40.

Example 7

3, 5, 4'-Tris (O-allyl)-trans-stilbene (7, Tri-O-allyl resveratrol)._Allylation of Resveratrol (1.0 g) by method 2 at r.t. (13 h), using Cs₂CO₃ (4.5 g) and allyl bromide (1.4 mL) in N,N-DMF (10.0 mL) gave 7 as the major product (R$_f$0.15, hexane-ethyl acetate 40:1 v/v) which was isolated after work up and column chromatography.

¹H-NMR, 6 (ppm, CDCl₃)._7.41 (d, 2p); 7.0 & 6.85 (2d=q, 2p); 6.89 (d, 2p); 6.65 (d, 2p); 6.39 (t, 1p); 6.05 (m, 3p, allylic CH— of O—CH₂—CH=CH₂); 5.41 & 5.25 (2d with multiple splitting, 6p, =CH₂ of O—CH₂—CH=CH₂); 4.55 (m, 6p, —OCH₂— of O-allyl). Ratio of aromatics from stilbene core and allylic protons, calculated and found matched at 9:15.

Example 8

Polycarbonates of THCCMN and its mixtures with CCMN, and BPA, respectively._Reactions were carried out according to the general scheme with each of the above stated bisphenols, individually and as mixtures (see table). Ratios used are representative and can be of any desired proportion. Reactions using suitable ratios of each were carried out according to the general method given above to give polycarbonates with properties listed in the Table below:

TABLE I

| Bis-Phenols/Ratio | Solubility | | | | M. Wt. | |
|---|---|---|---|---|---|---|
| | S1 | S2 | S3 | S4 | Mw | Mn |
| BPA | sp | s | s | ms | 5721 | 3117 |
| CCM | sp | sp | sp | sp | — | — |
| THCCM | s | s | s | ms | 2571 | 1555 |
| CCM:BPA/1:1.25 | s | s | s | Ins | 6219 | 2151 |
| THCCM:BPA/1:2 | s | s | s | sp | 3972 | 1753 |
| CCM:THCCM/1:2 | s | s | s | part | 6755 | 1982 |

S1: Acetone;
S2: Chloroform;
S3: N,N-Dimethylformamide;
S4: Methanol;
sp: Sparingly soluble;
s: Soluble;
ms: Moderate solubility;
Ins: Insoluble;
part: Part soluble when warmed Example 9

Polycarbonate of Resveratrol (RSVRTRL) using DPC (Molar ratio of RSVRRL:DPC 1:1.2)._Reaction carried out between RSVRTRL (1.6 g, 7.0 mM) and DPC (1.72 g, 8.03 mM), following the general method for making polycarbonates gave a foam that was powdered to give a off-white solid.

Example 10

Polycarbonate of Resveratrol (RSVRTRL) using DPC (Molar ratio of RSVRRL:DPC 1:3.3). Reaction carried out between RSVRTRL (1.5 g, 6.57 mM) and DPC (4.6 g, 21.48 mM), following the general method for making polycarbonates gave a hard solid that was broken up to give a white powder.

Example 11

Polyurethane using CCMN & MDI (1.2:1.0 molar ratio)._CCMN (1.0 g,) and MDI ((0.54 g) were weighed into a nitrogen purged, dry flask and dissolved in dry N,N'-DMF (8 mL). Into the clear solution was added catalytic quantity of DABCO (~5 mg) with stirring. Somewhat red, thick slurry formed shortly (5-10 min) which was transferred into cold 50% aqueous methanol, with vigorous stirring. A solid separated which was allowed to settle down while maintaining the solution temperature at 4° C. The solid was filtered and washed with 50%aq. methanol and dried under vacuum to give a yellow powder.

Example 12

Polyurethane using THCCMN & MDI (1.2:1.0 molar ratio)._THCCMN (0.84 g,) and MDI (0.44 g) were weighed into a nitrogen purged, dry flask and dissolved in a mixture of dry solvents N,N'-DMF (6 mL) and p-Dioxane (4 mL). DABCO (~0.5 mg) was added and stirring continued for 8 h at r.t. Reaction mixture was transferred into 50% aq. Methanol maintained at 4-7° C. A solid separated which was filtered, washed with cold 50% aq. methanol and dried under vacuum to give a white powder.

Example 13

Polyurethane using CCMN & MDI (1:1.2 molar ratio)._CCMN (1.05 g,) and MDI (0.83 g) were weighed into a nitrogen purged, dry flask and dissolved in N,N'-DMF (8 mL) and DABCO (~0.5 mg) was added and stirring continued for 8 h at r.t. A dark cake formed which was broken into small pieces, dispersed in cold ethanol (70 mL) and stirred at r.t. (8 h). Filtration, washing the solid with more ethanol and drying under vacuum gave a brown yellow solid.

Example 14

Polyurethane using THCCMN & MDI (1:1.2 molar ratio)._THCCMN (0.93 g,) and MDI (0.79 g) were weighed into a nitrogen purged, dry flask and dissolved in N,N'-DMF (10 mL) and DABCO (~0.5 mg) was added and stirring continued for 8 h at r.t. A gel had formed which was broken into small pieces, dispersed in cold ethanol and stirred at r.t. (8 h). Filtration, washing the solid with more ethanol and drying under vacuum gave a white spongy solid.

Example 15

Polyurethane using RSVRTRL & MDI (1:1.5 molar ratio): Reaction in N,N-DMF._RSVRTRL (1.02 g, 4.46 mM) was weighed into a nitrogen purged, dry flask and dissolved in N,N'-DMF (10 mL) to give a clear solution. MDI (1.64 g, 6.55 mM) was added and the mixture stirred at r.t. (30 min) and then at 40-45° C. while being stirred. Initially a gel formed which solidified. This material was broken up, transferred into a flask containing ethanol (75 mL) and vigorously stirred at r.t. (8 h). Filtration, washing the solid with more ethanol and drying under vacuum gave a ivory colored hard solid.

Example 16

Polyurethane using RSVRTRL & MDI (1:1.5 molar ratio): Reaction in p-Dioxane._RSVRTRL (1.01 g, 4.42 mM) was weighed into a nitrogen purged, dry flask and dissolved in p-dioxane (5 mL) and N,N'-DMF (1 mL). MDI (1.63 g, 6.51 mM) was weighed into another nitrogen purged, dry flask and dissolved in p-dioxane (50 mL) containing DCM (1 mL). The MDI solution was transferred into the flask containing RSVRTRL, DABCO (~5-8 mg) was added and the mixture stirred at r.t. (8 h). A soft solid formed which was broken up, transferred into a flask containing ethanol (75 mL) and vigorously stirred at r.t. (8 h). The solid was recovered by filtration and washed a second time by stirring in ethanol (r.t., 8 h). Filtration, and drying under vacuum gave a off-white powder.

Example 17

Polyurethane from a mixture of polyphenols: Use of RSVRTRL, THCCMN & MDI.

Method 1: RSVRTRL (0.5 g, 2.1 mM) and THCCMN (0.5 g, 1.34 mM) were weighed into a nitrogen purged, dry flask and dissolved in mixture of p-dioxane (5 mL) and N,N-DMF (0.3 mL). MDI (1.25 g, 4.9 mM) was weighed into another nitrogen purged, dry flask and dissolved in p-dioxane (50 mL) containing N,N-DMF (1 mL). The MDI solution was transferred into the flask containing RSVRTRL and THCCMN solution. DABCO (~5-8 mg) was added and the mixture stirred at r.t. A gelatinous mass formed which was broken up, transferred into a flask containing ethanol (45 mL) and vigorously stirred at r.t. (8 h). The solid was recovered by filtration and washed a second time by stirring in ethanol (r.t., 8 h). Filtration, and drying under vacuum gave a off-white powder.

Method 2: RSVRTRL (0.5 g, 2.1 mM) was weighed into a nitrogen purged, dry flask and dissolved in a mixture of p-dioxane (5 mL) and N,N-DMF (0.2mL). DABCO (~5-8 mg) was added followed by addition of a solution of MDI (0.275 g, 0.98 mM) in p-dioxane (6 mL) and N,N-DMF (1 mL). The reaction mixture was stirred (r.t., 10 h) followed by successive addition of a solution of THCCMN (0.5 g, 1.34 mM) in p-dioxane (3 mL) and MDI 0.955 g, 3.9 mM) dissolved in solvent mixture of p-dioxane (20 mL) and N,N-DMF (2 mL). Stirring was continued at r.t. (12 h). A gelatinous mass formed which was broken up, transferred into a flask containing ethanol (45 mL) and vigorously stirred at r.t. (8 h). The solid was recovered by filtration and washed a second time by stirring in ethanol (75 mL) at r.t. (8 h). Filtration, and drying under vacuum gave a off-white powder.

Example 18

Polymer composition: Polyurethane linked block polycarbonate of THCCMN._THCCMN (1.0 g) and DPC (0.6 g) was used to make a polycarbonate according to previously described method. The product, a mixture of oligomeric and polymeric carbonates having free OH, was dissolved in N,N-DMF (10 mL) and a solution of MDI (0.6 g) made in p-dioxane (15 mL) and N,N-DMF (1 mL) was added into it along with catalytic DABCO (5 mg). The mixture on being stirred at r.t. afforded a yellow solid which was broken and dispersed in ethanol (45 mL) and vigorously stirred at r.t. (8 h). The solid was recovered by filtration and washed a second time by stirring in ethanol (75 mL) at r.t. (8 h). Filtration, and drying under vacuum gave a off-white powder.

Example 19

Polymer composition using allyl carbonate derivatives of CCMN and THCCMN: Reaction with PETMA to give polymer composed of carbonate, ester and thio-ether linkages.

Reaction 1. Free radical mediated reaction between THC-CMN-di-allyl carbonate (506 mg, 0.94 mM) and PETMA (318 mg, 0.74 mM) was carried out at 90-95° C. in p-dioxane (8 mL) in presence of AIBN (20 mg). Within one hour a thick gel separated in a clear solution and TLC of the clear solution indicated absence of THCCMN derivative. Methanol (10 mL) was added and the reaction mixture stirred at r.t. (8 h). The spongy solid was isolated and dried under vacuum.

A second free radical mediated reaction using higher proportion of THCCMN-di-allyl carbonate (506 mg, 0.94 mM) and PETMA (212 mg, 0.49 mM) was carried out under same conditions to give a soft solid.

Reaction 2. Free radical mediated reaction between CCMN-di-allyl carbonate (550 mg, 1.02 mM) and PETMA (200 mg, 0.46 mM) was carried out at 90-95° C. in p-dioxane (8 mL) in presence of AIBN (12.5 mg). Within two hours a yellow slurry formed. TLC of an aliquot, dissolved in chloroform, indicated absence of PETMA and minor CCMN-di-allyl carbonate. Fresh AIBN (12 mg) was added and heating continued for one hour. The slurry was transferred into cold methanol (15 mL, 0-5° C.). The mixture on stirring produced light yellow solid in a turbid supernatant. Supernatant was discarded and the yellow powder dispersed in fresh methanol (20 mL), stirred vigorously (1 h) and filtered to get the solid product which was dried under vacuum.

A second free radical mediated reaction using higher proportion of PETMA was carried out using CCMN-di-allyl carbonate (510 mg, 0.95 mM) and PETMA (300 mg, 0.69 mM) in the presence of AIBN (20 mg). Heating at 95° C. (5 h) was followed by fresh addition of AIBN (10 mg) and reaction continued for another 12 h. The reaction mixture was cooled (5-10° C.) and a cooled solvent mixture, ethyl acetate-methanol (3:1 v/v, 25 mL), was added into the flask. A rubbery yellow mass formed which was separated, washed and dried under vacuum to give dark yellow brittle solid.

Example 20

Polymer composition using RTAC (Resveratrol triallyl carbonate): Reaction with PETMA to give polymer composed of carbonate, ester and thio-ether linkages.

A solution of RTAC (1 g, 2.08 mM) in p-dioxane (2.8 mL) was added into a solution of PETMA (0.9 g, 2.08 mM) in p-dioxane (10 mL) containing AIBN (27.4 mg) and reacted according to the general method described for free radical mediated reaction. Reaction mixture was heated (98-100° C.) for 4 h when a thick gel separated from a clear solution. The reaction mixture was cooled, solution was decanted and the gel was transferred into cold methanol (0-5° C., 20 mL). By this time a solid had formed which was broken up and the slurry stirred vigorously (1 h). The solid was recovered by filtration and washed a second time by stirring (4 h) in cold methanol (35 mL). Filtration, and drying under vacuum gave a white solid.

A second free radical mediated reaction was carried out under same conditions using 2:1 molar proportion of RTAC (1 g, 2.08 mM) and PETMA (450 mg, 1.04 mM). This produced a gummy material after the first methanol wash. This product was triturated under cold methanol during the second washing to afford a soft solid. Final filtration, washing with methanol and drying under vacuum gave a soft, white solid.

The invention claimed is:

1. A synthetic polymer comprising at least one monomer unit of at least one naturally occurring plant polyphenol or a derivative thereof.

2. The synthetic polymer of claim 1, wherein at least one chemical linkage of the polymer is carbonate, ether, carbamate, urethanes, thiocarbamate, thioether, or ester.

3. The synthetic polymer of claim 1 wherein the polymer is a homopolymer, co-polymer, block polymer, block co-polymer, grafted polymer, 3D polymer or interpenetrating polymer.

4. The synthetic polymer of claim 1, wherein at least one naturally occurring plant polyphenol is Curcumin, a hydrogenated curcumin (Tetrahydrocurcumin), Resveratrol, or hydrogenated Resveratrol (DH-Resveratrol).

5. A derivative of a plant polyphenol selected from the group consisting of Curcumin diallyl carbonate, Tetrahydrocurcumin diallyl carbonate, Resveratrol triallyl carbonate, Mono-O-allyl curcumin, Tetra-allyl curcumin, Di-allyl Tetrahydrocurcumin, Tetra-allyl Tetrahydrocurcumin, and Tri-O-allyl resveratrol.

6. A synthetic polymer comprising at least one monomer unit of a polyphenol derivative of claim 5.

7. The synthetic polymer of claim 6, wherein at least one chemical linkage of the polymer is carbonate, ether, carbamate, urethanes, thiocarbamate, thioether, or ester.

8. A method of making at least one derivative of a plant polyphenol of claim 5.

9. A method of making the synthetic polymer of claim 1.

10. A method of making the synthetic polymer of claim 6.

* * * * *

UNITED STATES PATENT AND TRADEMARK OFFICE
CERTIFICATE OF CORRECTION

| | |
|---|---|
| PATENT NO. | : 8,513,374 B2 |
| APPLICATION NO. | : 13/498886 |
| DATED | : August 20, 2013 |
| INVENTOR(S) | : Falguni Dasgupta |

It is certified that error appears in the above-identified patent and that said Letters Patent is hereby corrected as shown below:

On the Title Page

Change Item (76) Inventor to Item (75)

Below Item (75) of said Letters Patent insert

--(73) Assignee: INNOVOTECH, LLC, Bozeman, MT (US)--

Before Sheet 1 of drawings insert Chart 1

Signed and Sealed this
Twenty-sixth Day of August, 2014

Michelle K. Lee
*Deputy Director of the United States Patent and Trademark Office*

Chart 1: Natural Polyphenols

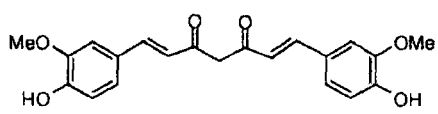

Curcumin (Source: *Curcuma longa*)

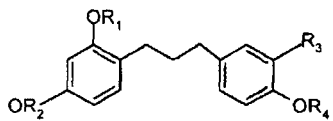

Broussonin A
$R_1 = R_3 = R_4 = H, R_2 = Me$
Broussonin B
$R_1 = Me, R_2 = R_3 = R_4 = H$
Broussonin C
$R_1 = R_2 = R_4 = H, R_3 = Prenyl$

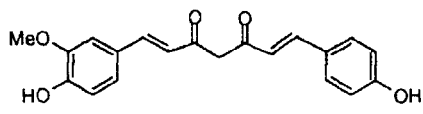

Desmethoxy Curcumin

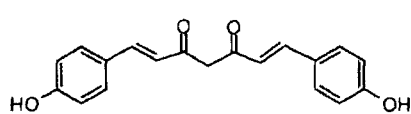

Bis-demethoxy Curcumin

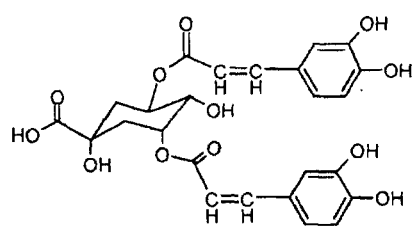

Cynarin

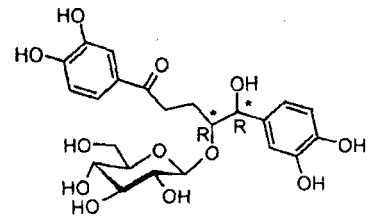

Curculigine (Source: *Curculigo orchioides*)

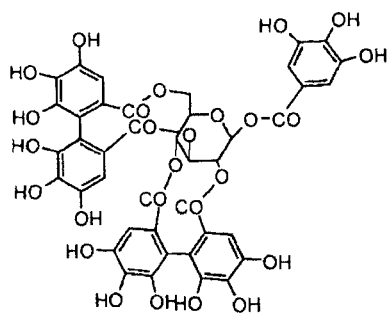

Chebulagic acid

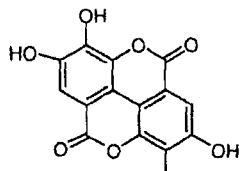

Ellagic acid (Source: Berries & Nuts)

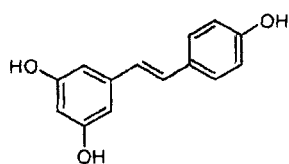

Resveratrol (Source: Red grapes, Berries, Eucalyptus, Peanuts, Spruce

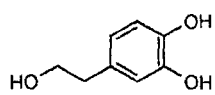

Hydroxytyrosol

Contd...Chart 1: Natural Polyphenols

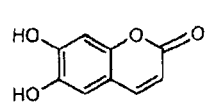
Aesculatin
Source: Berries & Nuts)

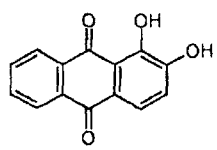
Alizarin (Mordant dye)
1, 2-Dihydroxy-anthraquinone

Chalcone

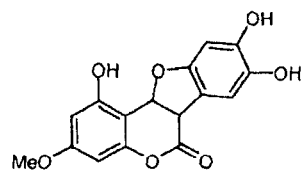
Wedelolactone
Source: *Eclipta alba*

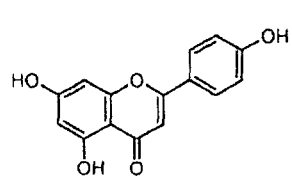
Apigenin (Flavone)

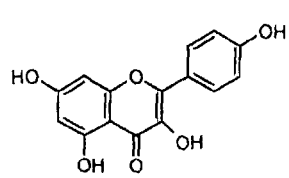
Flavonol

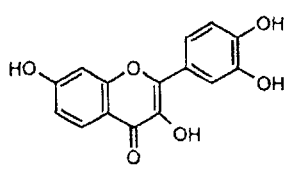
Fisetin
(Surce: Strawberry)

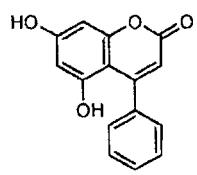
Neoflavonoids
(4-Phenyl coumarin)

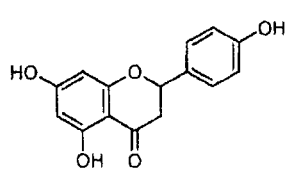
Flavonone

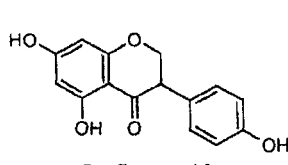
Isoflavonoid

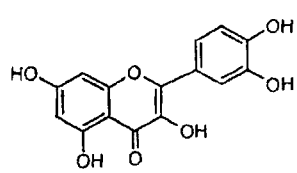
Quercetin, Source: Fruits, Vegetables, Nuts

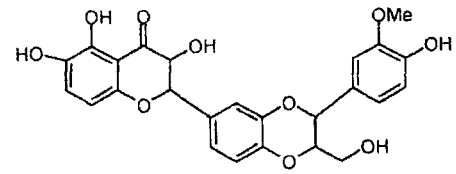
Silymarin (also, Silibinin; Source: Milk thistle, )

Contd...Chart 1: Natural Polyphenols
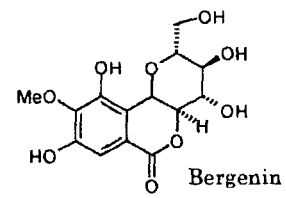
Bergenin
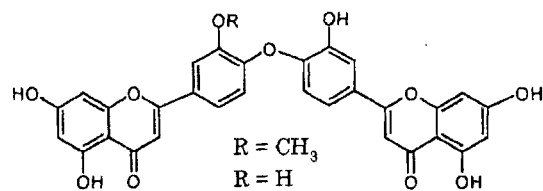
R = CH$_3$
R = H
Bioflavonoids / Bioflavonels
Source: *Parsley, Thyme, Peppermint, Basil, Celery, Artichoke, Lonicera japonica*
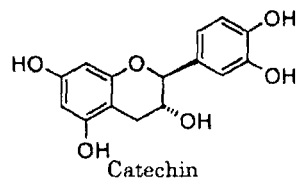
Catechin
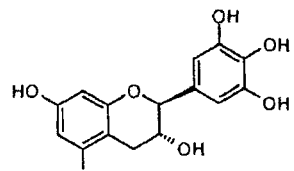
Gallocatechin
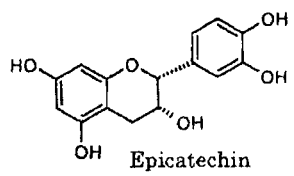
Epicatechin
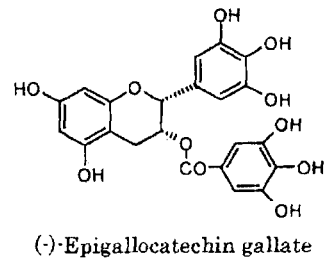
(-)-Epigallocatechin gallate
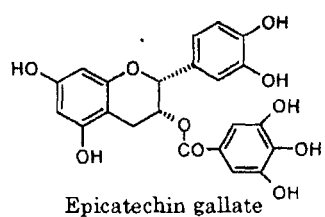
Epicatechin gallate
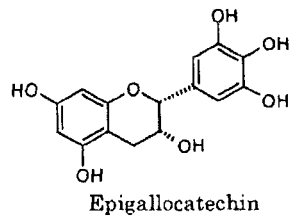
Epigallocatechin
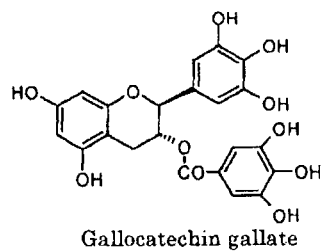
Gallocatechin gallate
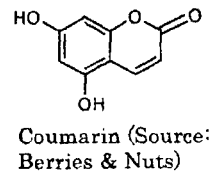
Coumarin (Source: Berries & Nuts)

CERTIFICATE OF CORRECTION (continued)
U.S. Pat. No. 8,513,374 B2

Contd...Chart 1: Natural Polyphenols

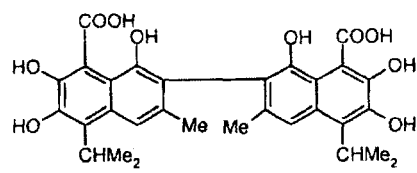

Gossypol (Source: Cottonseed; Plants of the *Gossypium genus, Malvaceae*)

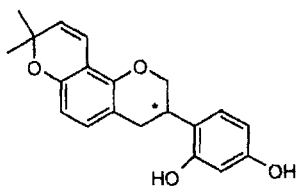

Glabridin (Source: *Glycyrrhiza glabra* Common name: Licorice)

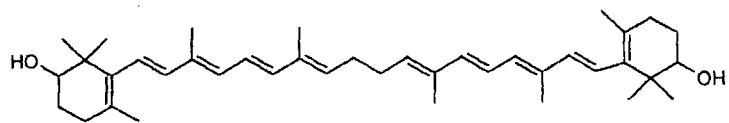

(2R, 2'R)-2, 2'-Dihydroxy-β-Carotene

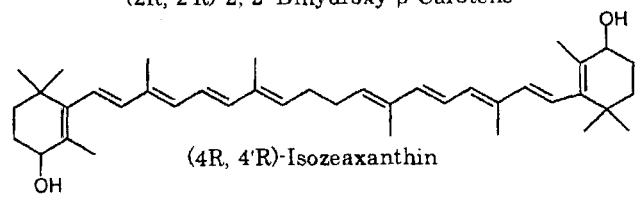

(4R, 4'R)-Isozeaxanthin

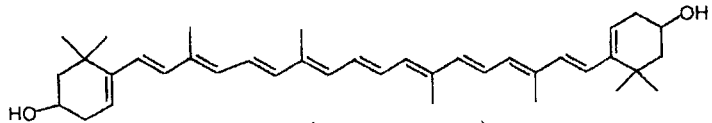

Lutein (Source: Tomato)

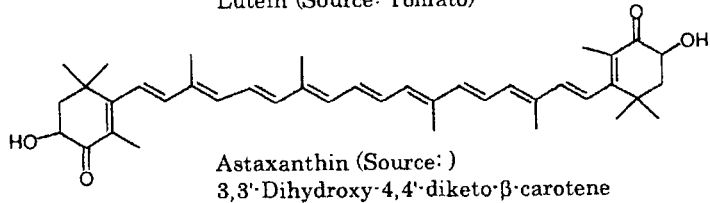

Astaxanthin (Source: )
3,3'-Dihydroxy-4,4'-diketo-β-carotene